(12) United States Patent  (10) Patent No.: US 9,109,981 B2
Sharp  (45) Date of Patent: Aug. 18, 2015

(54) METHODS AND APPARATUS FOR INDOOR AIR CONTAMINANT MONITORING

(71) Applicant: Aircuity, Inc., Newton, MA (US)

(72) Inventor: Gordon P. Sharp, Newton, MA (US)

(73) Assignee: AIRCUITY, INC., Newtown, MA (US)

( * ) Notice: Subject to any disclaimer, the term of this patent is extended or adjusted under 35 U.S.C. 154(b) by 333 days.

(21) Appl. No.: 13/834,719

(22) Filed: Mar. 15, 2013

(65) Prior Publication Data

US 2014/0260692 A1  Sep. 18, 2014

(51) Int. Cl.
G01N 1/22 (2006.01)
F24F 7/08 (2006.01)
F24F 11/00 (2006.01)

(52) U.S. Cl.
CPC .......... *G01N 1/2273* (2013.01); *F24F 11/0017* (2013.01); *F24F 7/08* (2013.01); *F24F 11/0001* (2013.01); *F24F 11/006* (2013.01); *F24F 2011/0002* (2013.01); *Y02B 30/78* (2013.01)

(58) Field of Classification Search
CPC .................................................. G01N 1/2273
USPC ............................................ 73/31.01, 31.02
See application file for complete search history.

(56) References Cited

U.S. PATENT DOCUMENTS

| | | | |
|---|---|---|---|
| 4,400,655 A | 8/1983 | Curtiss et al. | |
| 4,469,997 A | 9/1984 | Curtiss et al. | |
| 4,528,898 A | 7/1985 | Sharp et al. | |
| 4,706,553 A | 11/1987 | Sharp et al. | |
| 4,773,311 A | 9/1988 | Sharp | |
| 4,893,551 A | 1/1990 | Sharp | |
| 5,117,746 A | 6/1992 | Sharp | |
| 5,240,455 A | 8/1993 | Sharp | |
| 5,246,668 A | 9/1993 | MacCallum et al. | |
| 5,267,897 A | 12/1993 | Drees | |
| 5,292,280 A | 3/1994 | Janu et al. | |
| 5,293,771 A | 3/1994 | Ridenour | |
| 5,304,093 A | 4/1994 | Sharp et al. | |
| 5,385,505 A | 1/1995 | Sharp et al. | |
| 5,406,073 A | 4/1995 | Sharp et al. | |
| 5,435,779 A | 7/1995 | Sharp et al. | |
| 5,545,086 A | 8/1996 | Sharp et al. | |
| 5,831,848 A | 11/1998 | Rielly et al. | |
| 6,116,375 A | 9/2000 | Lorch et al. | |
| 6,125,710 A | 10/2000 | Sharp | |
| 6,137,403 A | 10/2000 | Desrochers et al. | |
| 6,241,950 B1 | 6/2001 | Veelenturf et al. | |
| 6,252,689 B1 | 6/2001 | Sharp | |
| 6,425,297 B1 | 7/2002 | Sharp | |
| 6,457,437 B1 | 10/2002 | Frasier et al. | |
| 6,609,967 B2 | 8/2003 | Sharp et al. | |
| 6,790,136 B2 | 9/2004 | Sharp et al. | |
| 7,216,556 B2 | 5/2007 | Desrochers et al. | |

(Continued)

OTHER PUBLICATIONS

PCT International Search Report and Written Opinion dated Nov. 10, 2014; for PCT Pat. App. No. PCT/US2014/013708; 14 pages.

(Continued)

*Primary Examiner* — Peter Macchiarolo
*Assistant Examiner* — Nathaniel Kolb
(74) *Attorney, Agent, or Firm* — Daly, Crowley, Mofford & Durkee, LLP

(57) ABSTRACT

Methods and apparatus for determining indoor air contaminant levels independent of outdoor contaminant levels. In one embodiment, an infinite geometric series is used to compute a true indoor air contaminant level in a room.

19 Claims, 5 Drawing Sheets

(56) References Cited

U.S. PATENT DOCUMENTS

| | | |
|---|---|---|
| 7,302,313 B2 | 11/2007 | Sharp et al. |
| 7,360,461 B2 | 4/2008 | Desrochers et al. |
| 7,389,158 B2 | 6/2008 | Desrochers et al. |
| 7,389,704 B2 | 6/2008 | Desrochers et al. |
| 7,415,901 B2 | 8/2008 | Desrochers et al. |
| 7,421,911 B2 | 9/2008 | Desrochers et al. |
| 8,147,302 B2 | 4/2012 | Desrochers et al. |
| 2006/0234621 A1* | 10/2006 | Desrochers et al. .......... 454/239 |

OTHER PUBLICATIONS

Invitation to Pay Additional Fees and Partial Search Report of the ISA for PCT/US2014/013708 dated Jun. 20, 2014.

* cited by examiner

METHODS AND APPARATUS FOR INDOOR AIR CONTAMINANT MONITORING

FIELD OF THE INVENTION

Exemplary embodiments of the invention provide methods and apparatus for air contaminant monitoring involving the use of either multipoint air sampling systems or discrete local air quality parameter sensors to sense one or more of air contaminants and air parameters to determine the amount of indoor air contaminants present in a given indoor space independent of the level of outdoor air contaminants that are being pulled into the building when said indoor space is being supplied by an air handling unit referred to as a return air handling unit that at least partially recirculates some of the indoor air back into the given indoor space instead of exhausting all of this return air. The determined level of indoor air contaminants may be used for information purposes only or to generate control signals to increase the supply airflows into the indoor space, increase outdoor air levels into said air handler or for other building control purposes.

Exemplary embodiments of the invention use filters in the air handling unit that reduce the level of sensed contaminant in the supply air to some extent less than about 100%. In one embodiment air contaminant comprises particulates and particularly the determination of the level of environmental tobacco smoke (ETS) particles in a space independent of total outdoor air particles. The control of room supply air and or outside air in the preferred embodiment would be for the purposes of dilution ventilation to control the level of environmental tobacco smoke (ETS) in indoor spaces or rooms.

BACKGROUND OF THE INVENTION

As is known in the art, there are various means for monitoring indoor environmental or air quality parameters. One approach involves the use of facility monitoring systems that are also referred to as multipoint air monitoring systems. A multipoint air monitoring system is defined as a monitoring system that includes one or more environmental or air quality parameter sensors to measure one or more air quality parameters in a plurality of locations that includes at least one location to measure the one or more air quality parameters in at least one room, space, partially enclosed area, or environment within a building, plus at least one other location to measure the one or more air quality parameters of the supply air feeding the room, space, partially enclosed area, or environment within the building. The latter location is typically a supply air duct or outlet of the air handling unit feeding the space room, space, partially enclosed area, or environment within the building. Other types of areas may be optionally sensed such as the return air and outside air inlets of the return air handling unit feeding said room or space.

As such, a multipoint air monitoring system may involve the use of one or more individual, discrete, local, wired or wireless sensors located in the space or area being measured. It may also use remote or centralized air quality parameter sensors that are multiplexed or shared amongst a plurality of spaces. Finally, a multipoint air monitoring system may use a combination of the previously mentioned remote and local air quality parameter sensors. Many examples of multipoint air monitoring systems are disclosed in U.S. Pat. No. 8,147,302 B2 entitled "Multipoint Air Sampling System Having Common Sensors to Provide Blended Air Quality Parameter Information for Monitoring and Building Control," which is incorporated herein by reference.

For those multipoint air monitoring systems where remote sensors are used, air is transported through a tube or pipe for sampling or measurement purposes. For example, a multipoint air monitoring system may have one or more centrally located air quality parameter sensors instead of distributed sensors local to the sensed environment. As such, this centralized air quality parameter sensor may be used in these systems to sense several or a large number of locations. These centralized air monitoring systems are also referred to as multipoint air sampling systems, or as multiplexed or shared sensor based facility monitoring systems.

Multipoint air sampling system are defined as specifically a facility monitoring system that uses shared or multiplexed sensor(s) comprising either a single remote sensor or a set of remotely located sensors used to monitor a plurality of spaces, areas or rooms within a building, or outside adjacent to a facility by transporting samples or packets of air from the spaces to be monitored to the at least one air quality parameter sensor.

For one class of these multipoint air sampling systems, a so-called star configured multipoint air sampling systems or just star configured systems, multiple tubes may be used to bring air samples from multiple locations to a centralized sensor(s). Centrally located air switches and/or solenoid valves may be used in this approach to sequentially switch the air from these locations through the different tubes to the sensor to measure the air from the multiple remote locations. Each location may be sensed for between ten seconds or several minutes. Depending on how many locations are sensed each space may be sensed on a periodic basis that could range from five to sixty minutes. These star configured systems are sometimes called octopus-like systems or home run systems and may use considerable amounts of tubing.

Systems such as this, for example, have been used to provide monitoring functions for the detection of refrigerant leaks, and other toxic gas monitoring applications. Other systems similar to this, such as that described within U.S. Pat. No. 6,241,950 to Veelenturf et al., which is incorporated herein by reference, disclose a fluid sampling system including a manifold having inputs, common purge and sampling pathways, and valves to couple/decouple first and second sets of inputs for measuring pressure differentials across sample locations.

Additionally, these types of star configured systems have been used to monitor particulates in multiple areas such as clean room areas with a single particle counter. A prior art example of this is a multiplexed particle counter such as the Universal Manifold System and Controller made by Lighthouse Worldwide Solutions, Inc., coupled with one of their particle counters such as their model number Solair 3100 portable laser based particle counter or an obscuration based particle sensor.

Regarding absolute moisture or dewpoint temperature measurement, an example of a prior art star configured multipoint air sampling system that can be used to measure dewpoint temperature is the AIRxpert 7000 Multi-sensor, Multipoint Monitoring system manufactured by AIRxpert Systems of Lexington, Mass., www.airexpert.com.

Another multipoint air sampling system defined as a networked air sampling system uses a central "backbone" tube with branches extending to various locations forming a bus-configured or tree like approach similar to the configuration of a data network. Air solenoids are typically remotely located proximate to the multiple sampling locations. The sampling time for each location like with the star configured systems may vary from about ten seconds to as much as several minutes. A typical sampling time per location would be about 45 seconds, so that with 20 locations sampled, each location could be sampled every 15 minutes. Networked air sampling systems can potentially be used to sample locations within a building, an air handling unit ductwork, exhaust air stacks of a building, or outside a building. An exemplary networked air sampling system is described in U.S. Pat. No. 6,125,710 to Sharp, which is incorporated herein by reference. U.S. Pat. No. 7,302,313 to Sharp et. al., titled "Air Quality Monitoring Systems and Methods", references different multipoint air monitoring systems including multipoint air sampling systems as used with expert system analysis capabilities and is also incorporated herein by reference.

Another multiplexed form of facility monitoring system is defined as a networked photonic sampling system that multiplexes packets of light vs. packets of air and may incorporate either a star configured or network/bus type of layout. The basic concept uses a central laser emitter and a central laser detector that sends out and detects laser light packets that are switched into rooms to be sensed by optical switches. Optical fiber sensors, infrared absorption cells or sensors, and other sensing techniques are located and used in the sensed area to change the properties of the light due to the affect of the environment. The light packet is then switched back to the central detector where the effect of the environment on the light properties is determined. A benefit of the system is that the sensors, such as fiber or open cell sensors, are potentially quite low in cost. The expensive part is the laser and detector systems that are centralized. Similar to the previous multipoint air sampling systems, multiple affects on the light from particles, gases and other contaminants, humidity, etc. can be done simultaneously with central equipment and the telecom concept of Wavelength Division Multiplexing which allows multiple wavelengths and hence multiple signals to share the same fiber. A clear advantage of this system is the ability to have a very rapid cycle time that can be in the tens of milliseconds or less. This sampling system is detailed in U.S. Pat. No. 6,252,689, entitled "Networked Photonic Distribution System for Sensing Ambient Conditions" and is incorporated herein by reference.

The multipoint air sampling systems and networked photonic sampling system which have been described heretofore and are collectively referred to as sampling systems may be applied to monitor a wide range of locations throughout a building, including any kinds of rooms, hallways, lobbies, interstitial spaces, penthouses, outdoor locations, and any number of locations within ductwork, plenums, and air handlers. To provide control as well as monitoring of these different spaces, virtual sensor signals can be created that refer to software or firmware variables, or continuous analog or digital signals that can be passed to other systems such as a building control or laboratory airflow control system and are representative of the state of a given space's air quality parameter value. In effect these signals are reflective of what a local sensor would read if it was being used instead of the multipoint air sampling system or networked photonic sampling system otherwise known collectively again as sampling systems.

Multipoint air sampling systems have been used with a wide variety of air quality parameter sensors to monitor a wide variety of air quality attributes or air characteristics of a building or facility. An air quality parameter sensor is a sensor that can detect one or more air quality attributes or parameters that convert the level of or information about the presence of an air quality parameter into either a continuously varying or else discontinuous pneumatic, electronic, analog or digital signal or else into a software or firmware variable representing the level of or information about the presence of an air quality parameter in a given space. The air quality parameter sensor may be based on any of a variety of sensing technologies known to those skilled in the art such as for example electrochemical, photonic or optical, infrared absorption, photo-acoustic, polymer, variable conductivity, flame ionization, photo-ionization, solid state, mixed metal oxide, ion mobility, surface acoustic wave, or fiber optic. The air quality parameter sensor may be a wired or wireless sensor type and be implemented with various types of physical hardware such as for example micro-electro-mechanical system based (MEMS), nanotechnology based, micro-system based, analog based, or digital based. Additionally, an air quality parameter sensor may sense for more than one air quality parameter, and may include more than one air quality parameter sensor in a single packaged device.

An air quality parameter is defined as an air characteristic that can include an air contaminant, an air comfort parameter, or carbon dioxide ($CO_2$). An air contaminant refers to certain potentially harmful or irritating chemical, biological, or radiological composition elements or properties of the air such as for example CO, particles of various sizes, smoke, aerosols, TVOC's (Total Volatile Organic Compounds), specific VOC's of interest, formaldehyde, NO, NOX, SOX, $SO_2$, hydrogen sulfide, chlorine, nitrous oxide, methane, hydrocarbons, ammonia, refrigerant gases, radon, ozone, radiation, biological and or chemical terrorist agents, other toxic gases, mold, other biologicals, and other contaminants of interest to be sensed. An air contaminant specifically does not refer to such other air quality parameters such as temperature, carbon dioxide, or any one of the many forms of measuring moisture or humidity in air such as for example relative humidity, dewpoint temperature, absolute humidity, wet bulb temperature, enthalpy, etc.

Furthermore, air contaminants can be further subdivided into two categories, gas based contaminants and particle based contaminants. Gas based contaminants are defined as air contaminants that are gas or vapor based such as CO, TVOC's, ozone, etc. Particle based contaminants on the other hand include viable and nonviable air borne particulate matter of any size, but generally of a particle size from 0.01 microns up to 100 microns in diameter. As such, this category of contaminants also includes biological particulate matter such as mold spores, bacteria, viruses, etc.

If these air contaminants are generated inside a building by indoor sources then they are referred to as indoor air contaminants, such as the environmental tobacco smoke (ETS) created by indoor smokers. If the air contaminants are generated by outdoor sources, such as from road dust, automobile exhaust, or particulates generated by burning coal or other fuels, even if they are pulled into the building such as by the air handling unit they are still referred to as outdoor air contaminants.

Carbon dioxide refers specifically to the gas carbon dioxide that is found naturally in the atmosphere as a component constituent in addition to oxygen and nitrogen. It is typically found in outside air at concentrations between 300 and 500 PPM and is exhaled by human beings at an approximate rate of 0.01 CFM per person for a person doing typical office work. Variations in the number of people in an office compared to the amount of outside air supplied into the building can easily vary indoor $CO_2$ levels to between 500 and 2500 PPM. As such $CO_2$ can be used as an excellent indicator of proper ventilation on a per person basis sometimes referred to as the CFM of outside air per person since the level of $CO_2$ in a space is directly related to the number of people in a space divided by the rise in $CO_2$ from outdoor levels. Although high $CO_2$ levels are often associated with poor indoor air quality levels, it is not the level of CO2 itself that creates the discomfort and symptoms associated with poor indoor air quality but instead the associated rise in air contaminants that are not being properly diluted. Human beings are unaffected by relatively high levels of CO2 such as up to 5000 PPM, which would be extremely rare to find in any building of ordinary construction.

An air comfort parameter specifically refers to either the measurement of temperature or one of the many related psychrometric measurements of moisture or humidity in air such as again, relative humidity, dewpoint temperature, absolute humidity, wet bulb temperature, and enthalpy. An air comfort parameter also does not refer to either carbon dioxide or any air contaminants. Additionally, an air quality parameter, air contaminant, or air comfort parameter specifically do not include any measure of airflow volume, velocity or pressure such as for example measurements of air volume that may be indicated in units of cubic feet per minute of air or other units, velocity pressure, air speed or velocity, static pressure, differential pressure, or absolute pressure.

Return air handling units are defined as air handling units that accept return air from the building where some portion of this air returned to the return air handling unit is mixed with some portion of outside air to provide a mix of return and outside air that may or may not be conditioned in some manner and then is provided as supply air to the various rooms or spaces served by the return air handling unit. The return air handling unit may or may not contain filters in the return, mixed air path, or supply airflow path that can reduce the level of air contaminants from the return air inlet of the air handler that are being delivered into the supply air stream. These filters if used may be either or both of particulate filters and gas phase filters.

The amount of air contaminants in the return air steam that pass into the supply air stream of the air handling unit will be reduced by one or both of two factors. The first factor referred to as the return air fraction is the percentage of return air that is not exhausted and is instead mixed with the outside air to constitute the supply air. For example a return air fraction of 25% would mean that 75% of the return air is exhausted and 25% is mixed with the outside air to create the return air handling unit's supply air. This means that 25% of the total contaminants in the return air stream will be fed into the supply air stream assuming no filtration.

The second factor relates to the issue of filtration. Filters located in the return, mixed air path, or supply airflow path will reduce the level of contaminants that are affected by these filters by the filtration efficiency. The filtration efficiency is defined as the percent of air contaminants that will on average be blocked by the return air handler's filters. Conversely, filtration porousness refers to the percent of air contaminants on average passing through the filters and is equal to one minus the filtration effectiveness. For example if for particulates, the return air handler has a filtration efficiency of 70% then the filtration porousness will be 30%. This means that 30% of the particulates of the return air will pass through the filter and 70% will be blocked or filtered out of the air stream. The filtration efficiency or filtration porousness can be measured for example by first measuring both the air contaminants levels entering the filter and the air contaminant levels leaving the filter. The filtration porousness is then equal to the level of contaminants leaving the filter divided by the level of contaminants entering the filter.

The term return air contaminant fraction is defined as the percentage of the total air contaminants present in the return air that will be passed into the supply air stream. For a given air contaminant, the return air contaminant fraction is equal to the product of the return air fraction and the filtration porousness for that air contaminant. When there is no filter in the return air handling unit or the filter that is used is not effective on the air contaminant (such as for a gas contaminant and a particulate filter), then the filtration porousness will be equal to one and the return air contaminant fraction will be equal to just the return air fraction.

There are many reasons that it is useful to sense the level of indoor air contaminants, such as for monitoring and safety purposes, or for the purposes of controlling the amount of dilution ventilation to eliminate or purge these contaminants from a space where they might have been generated. One known problem with sensing the level of indoor air contaminants such as for monitoring or for the control of dilution ventilation, particularly for such contaminants that are found commonly in outside air such as particles, CO, TVOC's or others, is that if the outside air concentrations become high enough, increasing the airflow volume of outside air or the supply air into a controlled area or room for purging or dilution ventilation will actually increase the sensed air contaminant levels in the controlled room or space. This can potentially create a negative feedback situation when the inside dilution ventilation threshold levels are exceeded forcing the outside airflow levels and or room supply air flow levels to their maximum level. Depending on the level of design capacity of the HVAC system, the capacity of the air handling system could be exceeded in this latch-up situation, causing a degradation of HVAC system control.

One solution to this problem of high outside air contaminant levels is disclosed in U.S. Pat. No. 8,147,302 B2 entitled "Multipoint Air Sampling System Having Common Sensors to Provide Blended Air Quality Parameter Information for Monitoring and Building Control" and is incorporated herein by reference. Rather than determining the indoor air contaminant levels by measuring the absolute level of air contaminants in a space; the '302 patent describes an approach of instead measuring the difference between the air contaminant levels in in the room and the air contaminant levels present in the supply air feeding that room. In this manner, the outdoor air contaminants present in the supply air were subtracted out from the levels of air contaminants measured in the room. By this method, the amount of indoor air contaminants generated in the room was calculated.

The above approach works when the air handler that is being used is a one pass or 100% outside air unit with no return air. As such, all the supply air is outside air and the simple differential measurement of room air minus supply air is fine. This approach also works reasonably well for some, although not all, cases where a return air handling unit is involved. The problem with return air handling units is that the contaminant that may be generated in a given space will be returned to the air handling units and some percentage of this contaminant will be then mixed with the outdoor air and then fed via the return air handling unit's supply air back into the original room plus into other rooms.

If the amount of contaminant generated in a space is small compared to the total air volume of the return air handling unit, or else the period of release of the contaminant in the room is relatively short in duration such as for much less than an hour, or the numbers of rooms where this release occurs is quite small percentage-wise since the release of contaminants may be for example quite uncommon, then the amount of total contaminant in the return air and hence the supply air will also be quite small. For these cases the simple differential measurement approach of above will still work reasonably well and give indoor contaminant concentrations with good accuracy.

However, if the sources of contaminant can be large, the period of release potentially long, or the number of spaces where the contaminant is generated can be a reasonable percentage such as over 10%, then the simple differential measurement method will likely produce inaccurate results. It can also cause significant problems when used for dilution ventilation when these conditions may be present.

The reason why the results will be inaccurate, is that when the return air has a potentially significant amount of contaminants present and a reasonable percentage of these contaminants are fed into the supply air this will mean that the supply air can have reasonable levels of both outside air contaminants as well as indoor air contaminants. When the simple differential method is performed all of the supply air contaminants are subtracted from the room air contaminants, both indoor and outside air portions. Thus the total amount of indoor air contaminant in the room will not be accurately calculated since it includes both the amount instantaneously generated in the space plus the amount returned to the space. Only the amount instantaneously generated in the space will be accurately measured. Unfortunately this is not sufficient for proper dilution ventilation control. For example, assume the return air fraction is high and even if filters are being used the filter's filtration porousness for the air contaminant is also high. In this situation a low contaminant generation rate creating a low differential between the supply and room contaminant levels might not trigger the need for more outside air. However, in this situation the background levels of the contaminant could grow quite high due to insufficient outside air yet it would not be detected by the simple differential measurement method.

As shown for example by U.S. Pat. No. 8,147,302 B2, this issue of finding the true level of indoor air contaminants independent of the outdoor air contaminant in a space is also not even recognized as a problem in the prior art.

Prior art approaches do exist to determine just the outside air fraction of an air handler. Note that the return air fraction is related to the outside air fraction in that the return air fraction is equal to one minus the outside air fraction. Regarding the determination of at least the outside air fraction, it could be measured directly or a mass balance calculation could be done using temperature or another tracer compound such as carbon dioxide. For this latter case, U.S. Pat. Nos. 5,292,280 and 5,267,897 describe a multipoint air sampling system that monitors a single trace gas, typically carbon dioxide (CO2), at multiple locations, including return air, outside air, and the supply discharge air associated with an air handler in order to directly compute the outside air fraction component for the purposes of controlling the return air handling unit. This method uses a common CO2 or trace gas sensor and valves assigned to each of the sampled locations to provide a multiplexed signal from the CO2 sensor that varies in time based on the current location being sampled. The time variant signal from the shared CO2 sensor is read by a separate control module, where it is decomposed into three separate CO2 or trace gas signals, based on continuous knowledge of the sequence state, representing outside air, return air, and supply discharge air CO2 concentrations. These signals are then used in a standard mass balance equation to determine the outside air fraction.

Even if the above patents disclosed how to determine the return air fraction, it is still not enough. Additionally, the return air contaminant fraction must be calculated which may also require determining the filtration porousness of the return air handling unit filters. However even this is still not a sufficient method. This is because a fraction of the air contaminants that return to the air handler will be sent back to the room in the supply air. The room air will then include newly generated contaminants plus a fraction of the previously generated contaminants. The new combined room air will subsequently be sent back again to the return air handling unit where a portion of the combined total return air contaminants will again be fed into the supply air. This set of contaminants will again go into the room where the newly generated contaminants will be added to what is now a fraction of the previous two sets of generated contaminants. As such the return air will go around and around and the indoor air contaminant level will potentially reach some sort of an asymptotic value after some period of time. This continuing recirculation of the contaminants involving the return air contaminant fraction makes the potential solution to determine the true indoor air contaminant levels no longer a simple difference calculation.

SUMMARY OF THE INVENTION

Exemplary embodiments of the invention provide methods and apparatus for determining indoor air contaminant levels independent of outdoor contaminant levels. In an exemplary embodiment, a system uses indoor air contaminant levels to create a dilution ventilation command signal and/or an outside airflow command signal. A dilution ventilation command signal is defined as an airflow command signal that can be used to vary, at least partially, the supply airflow rate into a monitored room or space based on sensed indoor air contaminant parameter information. The purpose of this control signal is to appropriately increase ventilation when air contaminant levels in a space or building are too high, typically to improve indoor air quality, and to decrease airflow levels, typically to save energy, when both the number of occupants in a space is reduced and the air is relatively clean of contaminants.

An outside airflow command signal is defined as an airflow command signal that can be used to vary, at least partially, the outside airflow into a building or air handling unit based on potentially multiple factors. These factors include, for example, the sensed air quality parameter information inside the building, the sensed air quality parameter information outside the building, the comparative levels of inside and outside sensed air quality parameters, the amount of free cooling to optimize energy efficiency and comfort, and the amount of outside airflow required to meet recommended guidelines based on the real time or design occupancy of for example the entire area of the building served by a particular return air handling unit, specific critical areas served by the return air handling unit, or areas served by the return air handling unit with varying occupancy. The purpose of this control signal is to balance energy savings from free cooling and demand control ventilation with providing enhanced indoor air quality through increased dilution of internal contaminants and preventing the excessive use of outside air when it is "dirty" or has excessive levels of air contaminants.

An airflow command signal refers to any pneumatic, electronic, analog or digital signal, or a software or firmware variable that operates in a firmware or software program running on a microprocessor or computer; and that is used by the room airflow controller, the outside airflow controller, the building control system, by one of the return, exhaust, or supply airflow control devices located in a room or space within the building, or by an outside airflow, recirculated airflow, or building exhaust airflow control device or damper often associated with a building's air handling unit or HVAC system. These command signals serve to at least partially vary or control one or more of the aspects of or relationships between any one of the airflows moving into or exiting the building, a return air handler or an area, space, room or environment within the building. If the airflow command signal is of a continuously varying nature it can be referred to herein as a VAV or variable air volume command signal. Otherwise, the airflow command signal may be a discontinuous airflow command signal defined as a signal that may have only two levels or states and is referred to as a two state signal, or it may have three levels or states and may thus be referred to as a three state signal. Alternatively, the discontinuous airflow command signal may have multiple discrete levels or states and as thus may be referred to herein as a multiple state signal.

A data or signal processing module or unit(s) refers to analog or digital electronic circuitry, and or a microprocessor or computer running a software or firmware program that may use information, signals and or software or firmware variables from any number of individual local sensors of air quality parameters, virtual sensor signals from an air sampling system, information and or software or firmware variables from remote or centralized sensors of air quality parameters. The data or signal processing units can blend, combine, compute, or process this information in a multitude of ways. As a result the data or signal processing units either create airflow command signals for building outside airflow control, for dilution ventilation, offset air volumes, or other airflow commands to be used by a room airflow controller, and/or for creating signals or information such as the indoor air contaminant signals or levels or the return air contaminant fraction that may be used by other control devices such as a building control system for at least partially controlling building level airflows including outside airflow into the building as well as one or more room airflows of supply, return, exhaust or offset airflow, and/or is used for some other control or monitoring purpose.

A building control system or building management system as mentioned above is defined as a control system located in a building or facility that is used to control one or more functions of the HVAC system in a building, such as for example, control of space temperature, space relative humidity, air handling unit airflows and operation, exhaust fan flows, chiller operation, economizer operation, duct static pressures, building pressurization, and critical environment airflows. These systems often integrate with or incorporate other building systems or subsystems such as fire and security, card access, closed circuit TV monitoring, smoke control systems, power monitoring, tracking airflow control systems, and critical environment airflow control systems. Building control systems may have pneumatic, electric, electronic, microprocessor, computer, or web based controls using pneumatic, analog and or digital signal inputs and outputs. These systems often have centralized monitoring functions, centralized or local control capabilities, and may have Internet or web based access. They may also be referred to as building management systems (BMS), facility control systems (FCS), or facility management systems (FMS).

Exemplary embodiments of the invention can provide systems and methods for creating indoor air contaminant measurements independent and unaffected by outdoor air contaminants thereby preventing dilution ventilation and outside airflow control from becoming latched up at high flow rates due to high outdoor levels of air contaminants. One embodiment using a multipoint air sampling system provides uniquely high accuracy to make this application possible since many differential measurements such as between room air contaminant levels and the supply air contaminant levels are made with the same sensor substantially reducing normal sensor errors that would typically be magnified when taking the difference between two different sensors.

In one aspect of the invention, a system for determining indoor air contaminant levels independent of outdoor contaminant levels comprises: an air contaminant monitoring system comprising: a first air contaminant sensor for collecting air contaminant levels from at least one partially enclosed area that is served by at least one return air handling unit that mixes at least a portion of building air returned to the air handler air into supply air, a second air contaminant sensor for collecting air contaminant levels from the supply air outlet of said return air handling unit, and at least one processor configured to: determine a return air contaminant fraction from the level of return air inlet contaminants of said return air handling unit that are present in said return air handling unit supply air outlet and the level of the air contaminants in the return air inlet, and process at least one indoor air contaminant parameter from: a magnitude of the difference between the air contaminant levels of said partially enclosed area and said supply air outlet of said return air handling unit feeding said partially enclosed area, and said return air handling unit return air contaminant fraction.

The system can further include one or more of the following features: the indoor air contaminant is a particulate, the particulate includes environmental tobacco smoke, the indoor air contaminant comprises a gas, the gas comprises a volatile organic compound, the air contaminant sensor is part of a multipoint air monitoring system, the multipoint air monitoring system is a multipoint air sampling system, the processor is further configured to determine the return air contaminant fraction by determining just the return air fraction comprising the percent of the total return air coming back to the return air handling unit that is being mixed with outside air to constitute the air handler supply air, the return air handling unit contains a filter in the return, recirc, mixed air, or supply air path capable of some amount of filtering of said air contaminant, the processor is further configured to: determine the return air fraction, determine a filtration porousness of the filter, and multiply the return air fraction by the filtration porousness to compute the return air contaminant fraction, determining the return air fraction comprises a one time or periodically measured set of flow measurements, mass balance measurements, or other manual means that are used to compute the return air fraction at least once or periodically, determining the return air fraction comprises automatic means to compute either continuously or periodically the return air fraction by using either flow sensing means, mass balance measurement means, or other automatic means, the processor is configured to perform a mass balance calculation and, the system further comprises a sensor to make carbon dioxide measurements representative of the carbon dioxide values in said return air handling unit return inlet, outside air inlet, and supply air outlet, determining the filtration porousness comprises: one or more air contaminant sensing means that senses an air contaminant that is filtered by the filter and takes a one time, periodic, and/or continuous air contaminant measurements of both the air before it enters the filter and the air after it leaves the filter, wherein processor is configured to compute the filtration porousness either one time, periodically, or continuously by dividing said air contaminant measurement of the air leaving said filter by said air contaminant measurement of the air entering said filter, determining the filtration porousness comprises: one or more air contaminant sensing means that senses an air contaminant that is filtered in some manner by the filter and takes a one time, periodic, or continuous air contaminant measurements representative of the air contaminant values in said return air handling unit return air inlet, outside air inlet, and supply air outlet, wherein the processor is configured to compute the filtration porousness either one time, periodically, or continuously by dividing said air contaminant measurement representative of the air contaminant values in said return air handling unit's supply air outlet by the sum of two terms, wherein, the first term is equal to the product of said return air fraction times said air contaminant measurement representative of the air contaminant values in said return air handling unit's return air inlet, and the second term is equal to the product of one minus said return air fraction times said air contaminant measurement representative of the air contaminant values in said return air handling unit's outside air inlet, at least one airflow control device to control airflow volume either to or from said at least one partially enclosed area, and an airflow controller that uses said indoor air contaminant parameter measurement or a signal at least partially determined by said indoor air contaminant parameter measurement to at least partially control airflow volumes to or from one or more of said partially enclosed areas, at least one airflow control device to control the outside air volume entering the outside air inlet of said return air handling unit, and an airflow controller that uses said indoor air contaminant parameter measurement or a signal at least partially determined by said indoor air contaminant parameter measurement to at least partially control the outside air volumes entering the outside air inlet of said return air handling unit, the processor is further configured to: take the magnitude of the difference between the air contaminant levels of said partially enclosed area and said supply air outlet of said return air handling unit feeding said partially enclosed area, and divide said difference by the term of one minus said return air handling unit return air contaminant fraction, the processor is further configured to: determine the magnitude of the difference between the air contaminant levels of said partially enclosed area and said supply air outlet of said return air handling unit feeding said partially enclosed area, and divide said difference by the term of one minus said return air handling unit's return air contaminant fraction, and/or at least one air contaminant sensor for collecting air contaminant levels from the return air inlet or duct of said return air handling unit, wherein the processor is further configured to: determine the magnitude of a first difference between the air contaminant levels of said partially enclosed area and said supply air outlet of said return air handling unit feeding said partially enclosed area, determine the magnitude of a second difference between the air contaminant levels of said return air inlet or duct and said supply air outlet of said return air handling unit feeding said partially enclosed area, determine the magnitude of a first factor calculated from said return air handling unit return air contaminant fraction divided by the term of one minus said return air handling unit return air contaminant fraction, and add said first difference to the product of said second difference multiplied by said first factor.

In another aspect of the invention, a method comprises: determining indoor air contaminant levels independent of outdoor contaminant levels by: using an infinite geometric series approximation having terms that include an air contaminant level generated by at least one source in a room, a return air fraction at an air handler unit, and filtration porousness to compute a true indoor air contaminant level in the room.

BRIEF DESCRIPTION OF THE DRAWINGS

The foregoing features of this invention, as well as the invention itself, may be more fully understood from the following description of the drawings in which.

DETAILED DESCRIPTION

Figure 1:
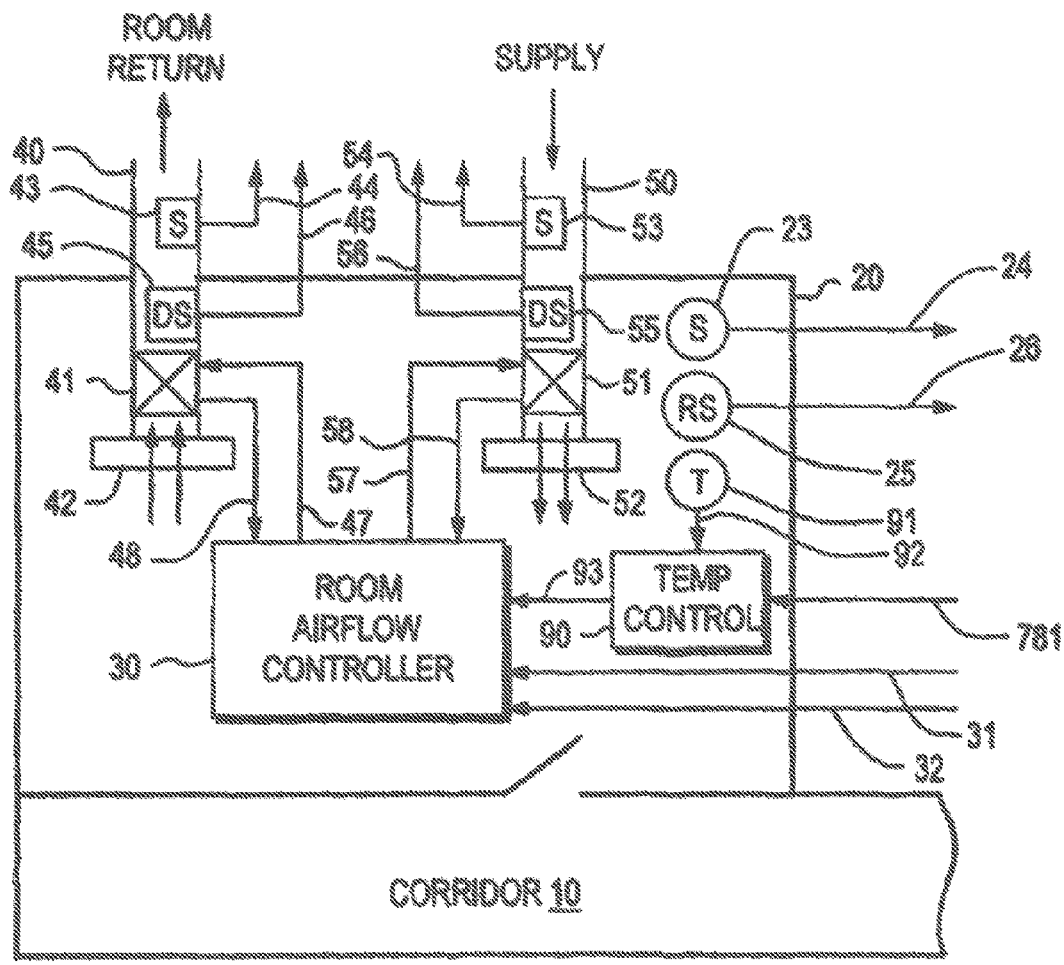
FIG. 1 is a detailed schematic diagram of a preferred embodiment of the system of the invention in a room which is being monitored for one or more indoor air contaminants and whose airflow may be controlled.

FIG. 1 show a typical monitored environment or room 20 that has doors that may enter a corridor 10 that may also be monitored. Although the diagrams show one room and a corridor, it is understood that exemplary embodiments of the invention may be used with just one room or space or monitored area, or any plurality of rooms or spaces including corridors or other adjacent spaces that are also being monitored, such as for example, two or more rooms, or one corridor plus one or more spaces. Note also that, although the illustrative environments are enclosed within walls, monitored environments, spaces or areas may also comprise a section or area of a room having no walls or partitions around it. Thus, there may be multiple monitored environments within one physical room. Alternatively, multiple physical rooms may also constitute one environment or space. Typically, the environment 20 will also be an area that is fed by one or more supply airflow control devices 51. Potentially a return airflow device 41 may be used that is controlled by room airflow controller 30 or there may be no controlled return air flow devices. In the latter two cases, the supply air may make its way back to a return air handler via a transfer duct or a ceiling grill into a plenum space that is typically in a ceiling space that eventually connects to the return airflow inlet of a return air handling unit such as return air handler unit 1000 in FIG. 2 that is providing the supply air into or near the space. It is understood that a room airflow controller such as room airflow controller 30 is an airflow control apparatus that may be of analog or digital electronic design or may be constructed using a microprocessor or computer running a software or firmware program that creates the airflow command signals for one or more supply and or return airflow control devices possibly using information, signals and airflow commands from other devices, systems or controllers.

Figure 2:
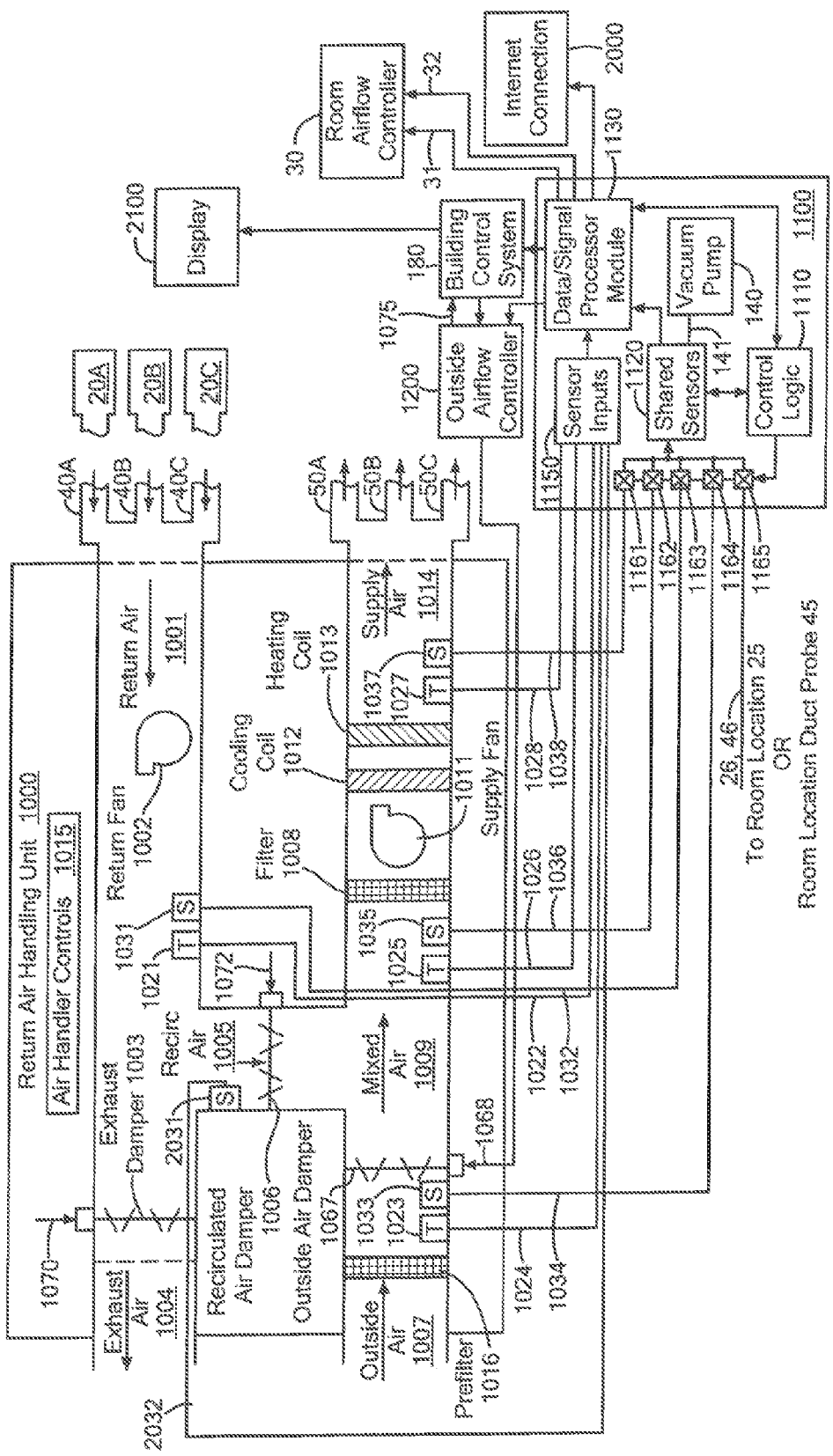
FIG. 2 is a schematic diagram of a preferred embodiment of the system of the invention in which a return air handling unit is being monitored by a multipoint air sampling system and where the outside air into the return air handling unit maybe controlled.

The room in FIG. 1 is further described as having a source of supply air from supply air duct 50, originating from air handler unit 1000 in FIG. 2, that may exit the room as return air through a plenum space or from controlled return duct 40, or an uncontrolled return duct or plenum space (not shown) through a room return grill or vent opening 42. Although not shown in the figures, the corridor 10 often has a source of supply air as well. The supply duct 50 also contains airflow control device 51 which provides supply air into the room or space through supply flow grill or diffuser 52 and is commanded by supply airflow control signal 57 and provides as an output the supply airflow feedback signal 58. Additionally, the room return duct 40 may or may not contain return airflow control device 41 which if used would control the amount of room or space air pulled into the return duct. If present, return airflow control device 41 is commanded by return airflow control signal 47 and provides as an output the room return airflow feedback signal 48.

As used herein, an airflow control device, such as supply or return airflow control devices 51 and 41 respectively are defined as any device known to those skilled in the art of airflow control for controlling air flow volume and velocity through a duct or opening. For example, they can be constant volume, two state, multiple state, or variable air volume (VAV) boxes or terminals such as manufactured by Titus, Metal Aire, Enviro-Tec, or others. These devices use a damper or throttling device of some type such as a single round, square, or rectangular blade damper, a multiple blade damper, a set of pneumatic bladders that can be used to seal off an opening, or any other type of throttling device that can be used to seal off a duct, that is connected to a pneumatic, electric, or electronic actuator that is controlled by a pneumatic, electronic, digital, or microprocessor based controller which typically also relies on feedback of flow from a flow sensor for closed loop control of the duct's air volume. These flow sensors can be of various types known to those skilled in the art, such as those based on single or multiple velocity pressure sensors, hot wire, heated thermistor, microelectronic flow sensor, etc.

Alternatively, another type of flow control device that is commonly used is an airflow control valve that typically has a venturi shaped body with a spring loaded cone that moves through the venturi shaped throat of the device to provide inherent, pressure independent control of volume, such as manufactured by Phoenix Controls or others. These valves typically have pneumatic, electric, or electronic actuation to provide constant volume, two-state, multiple state, or variable air volume control. These devices often have large turndown or flow ranges that make them very appropriate for control of dilution ventilation that can have wide flow ranges to achieve optimum energy savings and safety.

Finally, another example of an airflow control device may simply be some form of a single or multiple blade damper or other type of throttling device that is located either in an air handling unit, such as the dampers 1003, 1006, and 1067 in air handling unit 1000 in FIG. 2, an outside air duct, or a duct serving one or more areas. These throttling or damper devices may or may not further be used with one of the airflow measuring devices aforementioned or similar airflow measuring devices that are adapted using a grid of sensors or sensing holes for example to measure the airflow accurately across a large cross sectional duct area. As an example, outside airflow dampers providing airflow into an air handling unit are often not used in conjunction with an airflow measuring device. Alternatively, other indirect means of sensing the outside airflow may be used to provide better control of the outside airflow control device.

In FIG. 1, local temperature sensor 91 communicates through cable 92 to a temperature controller 90 that may have a temperature setpoint control signal 781 or is manually set. This temperature controller could be part of building control system, a stand-alone system, part of the room airflow controller 30, or part of a separate system that controls the airflow in a space or room with a return airflow control device. Such a latter control system that includes room return and supply airflow controller devices 41 and 51 respectively of FIG. 1, as well as the room airflow controller 30, and controls at least room pressurization by maintaining either a given room pressure or volume offset between the room and adjacent spaces is referred to as a tracking airflow control system which may also be used for example in critical environments, laboratories, hospitals, vivariums, and various types of clean rooms. In this latter case the room airflow controller 30 may also be referred to as a tracking airflow controller.

The purpose of temperature control block 90 is to provide regulation of room temperature which may involve sending a thermal load or temperature command 93 to the room airflow controller 30 to increase or decrease the volume of conditioned supply airflow into space 20. The temperature control 90 may also control a reheat coil to increase the temperature of the supply air fed into the space 20 or perimeter heating coils in space 20 for further means of temperature control.

Figure 3:
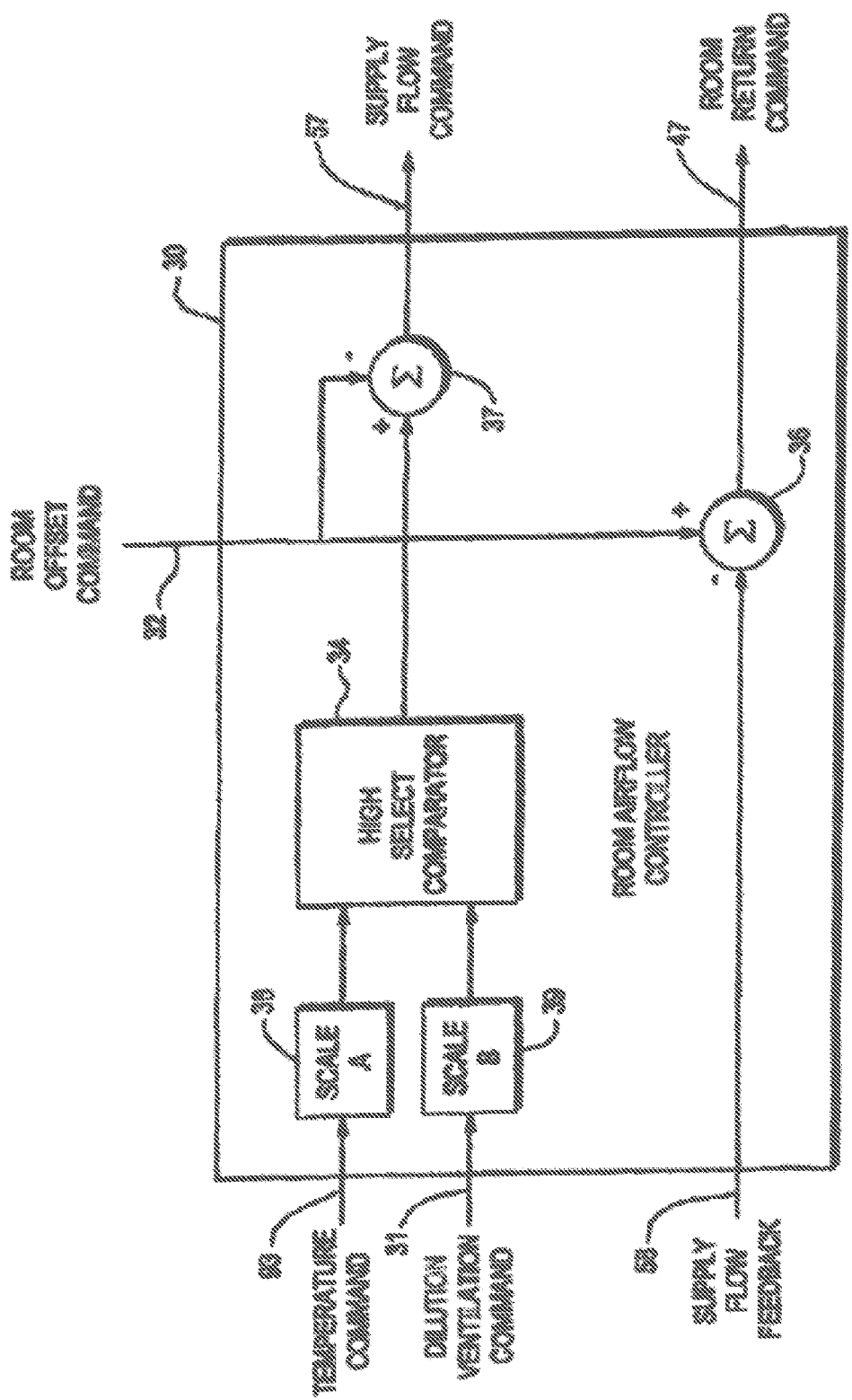
FIG. 3 is a schematic diagram of an embodiment of the room airflow controls logic of the invention for a space including a controlled room return airflow control device.

FIG. 3 is an exemplary embodiment of the control diagram for the room airflow controller 30. The supply airflow is set by the higher of either 1) the room's temperature control signal that represents the room's supply airflow requirement to maintain proper room temperature or 2) the dilution ventilation command signal that represents the supply airflow requirements for dilution ventilation based on the calculated indoor air contaminant levels in the space plus in some cases the volume of supply air required to meet the space's occupancy based on the measurement of space carbon dioxide levels. The minimum override or high select function for these two signals is implemented as shown in FIG. 3 by high select comparator Block 34 which acts to take the higher of the two signals provided to it, passing which ever of the two signals is higher at any given time. The first input into high select module 34 is the scaled temperature command 93 for varying supply flow. This signal is scaled and potentially offset as needed in scaling module 38 to put it on the same scale factor as the other airflow command signal input into high select comparator 34, such as to a certain number of cfm per volt for an analog voltage signal or scaled directly into a given set of units such as cfm or liters per second for a software or firmware variable representing airflow. The second signal into module 34 is the dilution ventilation command signal 31 which is generated by the data or signal processing unit of the multipoint air monitoring system, or is calculated by the building control system from sensed values in the room and in the air handler as is discussed later. This dilution ventilation command signal 31 is again scaled and offset as needed by scaling module 39 to put this command on the same scale factor as the other signal.

The command 57 for the supply airflow control device 51 is further shown created by taking the output of the high select comparator module 34 and subtracting offset signal 32 from it by subtraction module 37. The room offset airflow command 32 could be a fixed offset setpoint such as 10% of the maximum supply or exhaust cfm, or it could be a signal from the building control system, the multipoint air sampling system data or signal processing unit 1130 (FIG. 2) or the tracking airflow control system that varies in a two state, multistate or VAV fashion. The purpose of this offset airflow signal or variable 32, if it is used, is to create a typically slight negative, positive, or neutral pressure for rooms employing a room return or room exhaust airflow control device. If there is no return airflow control device used with the room than this control signal will not be employed.

This room offset control signal 32 may be used for example when a cleaning compound or other spill, or other emergency condition is detected such as a fire or smoke release via some sensor, alarm system, or manually with a room switch. In these cases the room offset airflow can be increased from its normal value by one of the controllers of the multipoint air sampling system 1100 (FIG. 2) or the building control system 180 (FIG. 2). Increasing the offset airflow to a potentially much higher value for example will reduce the supply airflow volume so as to create a large negative offset airflow for the room to provide a measure of increased containment to prevent the spread of potential spill vapors or smoke into other spaces.

FIG. 3 shows how room return command 47 for the room return airflow control device is created by first starting with the supply flow feedback signal 58. This signal 58 is next added to the room offset airflow command 32 by summation module 36. The resultant signal is the room return command signal 47 that is used to set and control the flow of the room return airflow control device 41.

Again, although a return airflow control device is indicated in FIG. 1, most buildings will only have a supply airflow control device controlled by the room airflow controller. If no return airflow control device is present in the room or area that is controlled by room airflow controller 30, then the control logic of the room airflow controller 30 is still applicable except that the room return airflow control device 41 and its signals 47 and 48, plus room offset command 32 and supply flow feedback signal 58, can be omitted. Furthermore, the supply flow command 57 equals the output of the high select comparator 34 with no subtraction block 37.

FIG. 2 shows an exemplary embodiment of the present invention directed to monitoring of indoor air contaminants or control of rooms or areas as well as the monitoring of air quality parameters in a return air handling unit using a multipoint air monitoring system with either or both of individual, discrete sensors as well as a star configured multipoint air sampling system with a structure like that described in U.S. Pat. No. 6,241,950; U.S. Pat. No. 5,292,280; U.S. Pat. No. 5,293,771 or U.S. Pat. No. 5,246,668. In other embodiment, a monitoring system includes a refrigerant and toxic gas monitor. A conventional refrigerant and toxic gas monitor is provided by the Vulcain Inc. multipoint sample draw gas monitor model number VASQN8X as can be seen on their website at www.vulcaininc.com or a multiplexed particle counter such as the Universal Manifold System and Controller made by Lighthouse Worldwide Solutions, Inc., as can be seen at their website at www.golighthouse.com, coupled with one of their particle counters such as their model number Solair 3100 portable laser based particle counter or an obscuration based particle sensor. It could also be a star configured multipoint air sampling system like that of the AIRxpert 7000 Multi-sensor, Multipoint Monitoring system manufactured by AIRxpert Systems of Lexington, Mass., as can be seen at their website at www.airexpert.com.

As shown in FIG. 2, return air 1001 for air handling unit 1000 comes for example from three rooms, which can be similar to room 20 of FIG. 1, or other areas, via return ducts 40A-C. As shown return air 1001 comes from return duct 40A from a first room, as well as from potentially a return air plenum space 40B which if fed by a ceiling grill 42B (FIG. 1) from a second room, and finally by return air from potentially a transfer duct 40C from a third room. Return air may also come from other locations or areas in the building. The supply air 1014 provided by air handling unit 1000 is provided to spaces in the building such as the three rooms through supply ducts 50A, 50B, and 50C respectively. Although not shown, other areas or rooms of the building such as for example corridor 10 may also be supplied by air handler unit 1000. Return air fan 1002 and supply air fan 1011 are used to move the air through the building. Prefilter 1016 is typically used in the location shown and is often a coarse filter that is used on the outside air stream. This is followed by a typically more effective and higher grade filter shown as filter 1008. Control of the temperature and humidity content of the supply air can for example be controlled through cooling coil 1012 and heating coil 1013. Other combinations of filters and heating and cooling coils used with respect to a return air handling unit or similar roof top units for meeting various applications are well known to those skilled in the art of designing air handling units.

Additionally, the control of the amount of recirculated return air 1005, exhausted return air 1004, and outside air 1007 is through the control of exhaust air damper 1003, recirculated air damper 1006, and outside air damper 1067. These dampers can also be airflow control devices as defined earlier for such devices as 41 in FIG. 1 although the dampers or airflow control devices in FIG. 2 will typically be larger devices due to the larger air volumes involved. The control signals to control these dampers are shown in FIG. 2 as outside air damper control signal 1068, exhaust air damper control signal 1070, and recirculated air damper control signal 1072. There are many techniques known to those skilled in the art to control the relative positions of these dampers. Typically, the building control system 180 or an air handler controls unit 1015 will control these dampers to meet various requirements of the building such as regarding the required amount of outside air, matters of energy efficiency relating to the heating and cooling of the building, and building pressurization.

To monitor the operation of the air handling unit 1000 to help calculate the indoor air contaminant levels of a room 20 supplied by the return air handler unit 1000 as well as to potentially control the amount of required outside air to dilute the indoor air contaminants in the building, several air handler locations can be monitored with the use of a multipoint air sampling system such as that shown in FIG. 2 as block 1100. Multipoint air sampling system 1000 can be provided as a star configured multipoint air sampling system. In other embodiments, a networked air sampling system is provided.

In FIG. 2, as a part of the multipoint air sampling system, a set of solenoid valves 1161 through 1165 is part of a multipoint air sampling system 1100. Equivalently, these solenoids 1161 through 1165 could be replaced with other switching means such as SSS-48C Single Scanivalve System manufactured by the Scanivalve Corporation of Liberty Lake, Wash. as can be seen on their website, www.scanivalve.com, which uses a pneumatic selector switch and stepper motor to connect one of many input ports to an outlet port which can be connected to a sensor such as a pressure sensor. The solenoid valves 1161 through 1165 are controlled to switch in a sequence by control logic 1110. This sequence may be a simple sequential pattern of one solenoid after another, or varied for example through programming to be one of potentially many preset patterns, or it can have a pattern that can be interrupted and changed to a new sequence by manual or remote command or by a trigger event based.

To monitor operation of the air handler and to better control it, one of the sense locations as shown in FIG. 2 involves sensing the return air 1001 either before or after the return fan 1002 with air sampling location 1031 and or alternatively local duct air contaminant, airflow volume, or air quality parameter sensor 1021. Another sense location involves sensing the supply air typically after the fan and various heating and cooling coils to better ensure a more homogeneous distribution of temperature and air contaminants within the supply duct. This is shown in FIG. 2 with sampling location 1037 and or alternatively local duct sensor 1027 which could be a discrete air contaminant, air flow volume, or air quality parameter sensor. Alternatively the supply air can also be sensed at a duct location near the room 20. FIG. 1 shows one of these supply duct sampling locations 55 which can be connected the multipoint air sampling system via tube 56. A discrete air quality parameter or air contaminant sensor 53 is also shown and can be connected to the sensor inputs block 1150 via cable 54.

Another sense location potentially used in this invention involves sensing outside air. In FIG. 2 outside air 1007 is sensed for example in the outside air duct by air sampling location 1033 and local duct air contaminant, airflow volume, or air quality parameter sensor 1023 after the prefilter 1016 (if used) and either before or after the outside air damper 1067. Other outdoor air measurement locations such as an area outside that is reasonably representative of the outside air that is drawn into the return air handler's outside air inlet is also a good sensing location assuming that the prefilter 1016 if used will not appreciably affect the air contaminant measurement. Finally a location that may also be helpful to sense in the return air handling unit is in the mixed air plenum of the air handler where the mixed air 1009 of the air handler is present. This air is similar to the supply air but has not been filtered, heated or cooled by the air handler so it more closely reflects the mixed air quality parameter characteristics of the return air 1005 and outside air 1007. The mixed air 1009 is sensed by air sampling location 1035 and local duct air contaminant, airflow volume, or air quality parameter sensor 1025. It is useful to note that care must be taken with the selection of the air sampling and or duct sensor locations in the mixed air plenum. In many air handlers the return and outside air may be poorly mixed in the mixed air plenum before filter 1008 resulting in a non homogenous air contaminant and temperature distribution due to the different values present in the return and outside air.

Another location for a local or discrete duct air contaminant, airflow volume, or air quality parameter sensor is the recirc air sensor location 2031 which is connected to the sensor inputs block 1150 through cable 2032.

With respect to the sensed duct locations, when multipoint air sampling systems are used to sample ductwork, plenums, air handlers or any other applications where flowing air in a partially contained area such as a duct or pipe is to be sampled and measured with a remote sensor, a tube or hollow duct probe may be inserted into the duct or partially contained space to withdraw a sample or else a hole can be made in the duct and a sample drawn from the duct from a tube connected to the opening in the duct wall. Additionally however, as noted above a separate temperature, airflow volume, air quality parameter, or air contaminant sensing probe, probes, or discrete air quality sensor or sensors may also be used to make whatever local sensor measurements are desired from these ducts or partially enclosed areas. Multiple separate probes for both sensing the flowing air stream and for drawing air samples may be employed at these locations or a unique integrated sampling probe that uses one probe for both local air characteristic measurements and for air sampling may be used as described in the U.S. Pat. Nos. 7,415,901 and 7,415,901, entitled "DUCT PROBE ASSEMBLY SYSTEM FOR MULTIPOINT AIR SAMPLING" which is incorporated herein by reference. This type of integrated duct probe or other nonintegrated duct probes may be used to sense any of the duct locations referred to in FIG. 2. Additionally, exemplary embodiments can use air sampling duct probes that use multiple sensing holes spread along a cross section of the duct to obtain a better average of duct conditions. This type of multiple pickup sampling probe plus an averaging duct temperature sensor that is also described below may be used advantageously for example to measure the mixed air 1009 of the air handler.

A fifth location that also can be sensed is a location that will give a measurement representative of the air contaminant levels in the room or space 20 that is being monitored. Two locations that can be used depending on the characteristics of the space are either the return duct location 45 (FIG. 1) which can be used is there is a return duct coming out of the room or space, or otherwise when there is no return duct from the room, since for example it uses an open plenum return, then a good location is the sense location 25 which may be a wall, column or even a ceiling mounted room sensing location. Note that these room sensing locations can be used even if there is a return duct. Air sampling tubes 46 and 26 are used to connect sensed locations 45 and 25 respectively to the multipoint air sampling system 1100. Note that alternatively the return air duct and room locations can also be sensed with individual or discrete sensors 43 and 23 respectively and connected instead via wires 44 and 24 to the sensor inputs block 1150.

As shown in FIG. 2 multipoint air sampling system 1100 accepts the other four previously mentioned air sampling locations that are connected to the solenoid valves 1163, 1164, 1162, and 1161 by air sampling tubes 1032, 1034, 1036, and 1038 from sampling locations 1031, 1033, 1035, and 1037 respectively. This tubing transports the air sample from the sensing location to the solenoid of the multipoint air sampling system 1100. The tubing typically will have an inner diameter of one eighth to one half an inch in diameter with a preferred inner diameter of about one quarter inches. This tubing can be made of standard plastic pneumatic tubing such as Dekoron™ low density polyethylene (LDPE) plastic, Teflon, stainless steel, "Bev-A-Line XX" tubing made by Thermoplastic Processes, Inc. of Stirling, N.J., or other suitable tubing materials known to those skilled in the art. For superior performance in transporting both TVOC's and particles however, a material that is both inert to VOC's with very little adsorption and desorption as well as electrically conductive to prevent static buildup is preferred such as flexible stainless steel tubing. Other preferred materials and constructions are described in U.S. Pat. No. 7,216,556 entitled, "TUBING FOR TRANSPORTING AIR SAMPLES IN AN AIR MONITORING SYSTEM", as well as U.S. Pat. No. 7,360,461 entitled, "AIR MONITORING SYSTEM HAVING TUBING WITH AN ELECTRICALLY CONDUCTIVE INNER SURFACE FOR TRANSPORTING AIR SAMPLES".

Additionally in FIG. 2, a vacuum pump 140 pulls air from the sensing locations through the tubing into the solenoids 1161 through 1165 and into a manifold connecting all the output ports of the solenoids together and to the inlet of the shared sensors 1120. The outlet of the shared sensors 1120 is connected to the vacuum pump 140 by tubing 141. The inner diameter of this tubing 141 can be made similar to the size of the tubing connecting to the inlets of the solenoid valves or possibly larger for less pressure drop. The shared sensors 1120 can include one or more sensors to measure such air comfort parameters as absolute humidity or dewpoint temperature, carbon dioxide, non-air quality parameters such as differential static pressure, or air contaminants such as for example, CO, particles, smoke, TVOC's, specific VOC's of interest, formaldehyde, NO, NOX, SOX, nitrous oxide, ammonia, refrigerant gases, radon, ozone, biological and or chemical terrorist agents, mold, other biologicals, and other air contaminants of interest to be sensed. These sensors may be connected in series, in parallel or a combination of both.

The air quality parameters at these air handler locations are sensed by the shared sensors 1120 and processed by the data signal processing module 1130 which can implement the functionality described below to calculate the indoor air contaminant levels. The solenoids 1161 through 1165 are also controlled by control logic module 1110. Further, multipoint air sampling system 1100 can accept local room or duct sensor signals or information through sensor inputs module 1150, which senses local duct air quality parameter sensors 1021, 1023, 1025, 1027, and 2031 through electrical signal cables 1022, 1024, 1026, 1028 and 2032 respectively. These cables are similar to low voltage signal cable or twisted shielded conductor pairs that are commonly used in building control systems to connect sensors to the control system. Alternatively, local duct sensors 1021, 1023, 1025, 1027, or 2031 may communicate their air contaminant, air quality parameter or airflow volume information to sensor inputs block 1150 through wireless or wireless network means such as a wireless mesh network.

The above shared sensors 1120 and discrete air contaminant, air quality parameter or airflow volume sensors 1021, 1023, 1025, 1027 and 2031 may operate with many signal forms such as analog voltage, analog current, or digital. Alternatively, the sensor may have its own onboard microprocessor and communicate with the data or signal processing unit 1130 through a data communications protocol such as, for example, LonTalk by Echelon Corporation, or an appropriate protocol outlined by ASHRAE's BACnet communications standards, or virtually any other appropriate protocol, including various proprietary protocols and other industry standard protocols commonly used to provide data communications between devices within a building environment.

The control or monitoring signal outputs of data or signal processing unit 1130 can be provided for example to building control system 180 as shown, for control of the outside air damper 1067 or to other building systems or controllers such as the air handler controls block 1015 or more specifically to the outside airflow controller module 1200 which can be used to generate outside airflow command signal 1075 using traditional control loop technology as is known in the art such as proportional; proportional and integral; or proportional, integral, and derivative control logic algorithms. Although not shown in FIG. 2, the building control system 180, the air handler controls block 1015, or another controller can be used to control the outside airflow into the building using outside air damper 1067 plus additionally the other air handler dampers 1003 and 1006 with the help of the outside airflow command signal 1075 from the outside airflow controller 1200.

Another potential control output of the data or signal processing unit 1130 is to produce dilution ventilation command signal 31 either directly or through the building control system 180 after it acts upon output signals from the data or signal processing unit 1130. Generally when the data or signal processing unit 1130 calculates the one or more indoor air contaminant signals as described later and one or more these signals exceed a given threshold or other trigger condition then the dilution ventilation command signal 31 is increased by room airflow controller 30 to increase the supply airflow into the monitored space 20 to dilute the one or more air contaminants that have been sensed.

As with the outside airflow command signal 1075, There are a number of control techniques that may be used to generate command 31 in order to vary the amount of ventilation within the monitored environment 20 in order to dilute the sensed air quality parameter sufficiently to prevent the concentration of the airborne air quality parameter from exceeding a specific level. Any method that one may use, from a standpoint of control logic, whether it be an open or closed loop strategy involving continuous or discontinuous control functions, fuzzy logic, proportional-integral-derivative functions, feed-forward functions, adaptive control, or other techniques known to those skilled in the art of control system design, are considered to be within the scope of the claimed invention.

In addition to a two state control output signal, another preferred type of signal and related control approach for creating and using dilution ventilation command signals 31, outside airflow command signal 1075, or the control signal output 1068 of outside airflow controller 1200 is to use continuously variable signals that can be used to implement a variable air volume or VAV control approach. With this signal type and control approach, once the calculated indoor air contaminant levels or signals calculated by the data or signal processing unit 1130 reach some trigger level or match some signal pattern, the dilution ventilation command signal 31, outside airflow command signal 1075, or the control signal output 1068 of outside airflow controller 1200 can increase in a continuous manner from a minimum level which would match the minimum state output of a two or multiple state approach, all the way up to a maximum level that would correspond to the maximum level of a two state or multiple state approach Another of the reasons to use a continuously variable signal state is to create closed loop control of the indoor environmental quality within the monitored space or building so as to prevent an oscillating control pattern that might be generated in some situations by a two state or even a multi-state approach. With a continuously variable signal state a variable air volume (VAV) control approach can be implemented so that an increased ventilation level can be maintained in a stable manner between the minimum and maximum command signal levels, particularly where there is a roughly constant level of indoor air contaminant emission such as for example from environmental tobacco smoke generated by one or more smokers in the room 20. This approach could be used to regulate the level of an indoor air contaminant parameter such as a TVOC, particulate, or other at a certain setpoint rather than drive it to a minimum level that could prove to be costly in terms of the energy expense of running at high ventilation for extended periods. This approach is also appropriate when the indoor air contaminant parameter is either not a particularly hazardous one or there are stated or regulatory threshold limits on these air contaminant levels. In these cases the dilution ventilation or outside air airflow levels can be maintained at a level that would either not create a health impact or maintains the levels below the regulatory or stated threshold limits. More particularly, by generating a dilution ventilation or outside airflow control signal from one or more indoor air contaminant parameters that is independent of outside air contaminant levels, the indoor environmental quality in a space can be maintained to a given "cleanliness level" with respect to these indoor air contaminants independent of the outdoor air contaminant levels.

Another potential control output of the data or signal processing unit 1130 is to produce room offset command signal 32 either directly or through the building control system 180 after it acts upon output signals from the data or signal processing unit 1130. As with dilution ventilation command signal 31 this signal can be used to adjust the ventilation of room 20 advantageously when certain indoor air contaminants are sensed.

In addition to or instead of just creating air flow control signals, the data or signal processing unit 1130 may also be used for calculating indoor air contaminant level measurements for monitoring or information purposes. This information may be viewed locally from the system directly or the information can be sent to the building control system 180 through an analog or a digital connection using protocols such as LON or BACNet and displayed on a monitor or display 2100. The data or signal processing unit 1130 may also send this indoor air contaminant information and data to the Internet 2000 where remote servers can then collect, archive, analyze and or send information to a user located anywhere in the world.

One of the beneficial advantages creating an indoor air contaminant signal independent of outdoor air contaminant levels relates to not only getting accurate information for monitoring of the indoor air contaminant levels, such as smoke particle levels, but also solving a potential problem with the room dilution ventilation control and outside air control approaches mentioned above. The issue is that outside air that is being brought into the building may become slightly or significantly contaminated by one or more air contaminants. Such air contaminants could include carbon monoxide from auto or truck exhaust or from re-entrainment of furnace or boiler exhaust, high levels of outdoor particulates, TVOC's that could be re-entrained from nearby exhaust stacks, or other outdoor sources of air contaminants. If these air contaminants are not filtered out completely and pass into the supply air that is being fed into the rooms it could trigger the dilution ventilation controls to increase the supply air flows and or the outside air flow from the outside air intakes inappropriately. Similarly, the increase in supply air contaminants may not be high enough to trigger increased supply air or outside air flow commands by itself, but added to existing air contaminant levels in the room or building it may make the system overly sensitive to low or moderate air contaminant levels originating from within the room or building. Both of these problems can produce potentially runaway results since the control action of increasing supply or outside air which contains air contaminants only serves to increase the level of the particular air contaminant within the room or building. This can drive the supply or outside airflow levels even higher until no matter whether a two state, three state, or VAV approach is used the supply airflow into the room or the outside airflow into the building will eventually be commanded to its maximum level if the outside air or supply system contamination is high enough. Since the supply system airflow potentially feeds many rooms, potentially all of these rooms could be pushed to their maximum flows or else the amount of outside air being drawn into the building could reach potentially as high as 100% outside air. This could result in the airflow capacity and or the heating and cooling capacity of the supply system being exceeded with potential resultant reductions of flow into the room spaces and also potential loss of temperature control of these spaces if the temperature of the conditioned supply air can not be appropriately controlled due to an excessive amount of outside air being drawn into the building.

In a building where 100% outside air is being used and no or very little return air is used or where the contaminant from any given space is small and will not impact the amount of contaminant in the supply air then a control approach can be used as is disclosed in U.S. Pat. No. 8,147,302 B2 entitled "Multipoint Air Sampling System Having Common Sensors to Provide Blended Air Quality Parameter Information for Monitoring and Building Control". In this approach an outside air or supply air measurement is subtracted from room air measurements to create differential measurements of the various air contaminants of interest vs. either outside air or the supply air. Thus, if the outside or supply air has an increase in particles, CO, TVOC's, etc., the air quality of the room air will be evaluated against sources of air contaminants in the room only since the effect of the supply air sources will be subtracted out. Effectively, we are concerned here not with the absolute air quality of the room air but whether it is being made worse by sources in the room or space only, since increasing the supply or outside air will not make the room air cleaner if the supply or outside air is the source of the air contaminant.

If the return air from one or many spaces has a potentially large amount of contaminants, the period of release potentially long, or the number of spaces where the contaminant is generated is a reasonable percentage, such as over 10%, then the supply air may likely have a significant amount of contaminants that have passed into the supply air from the return air at least with respect to air contaminant threshold levels. For these cases the above mentioned prior art differential measurement approach will not work correctly. This is because the indoor air contaminant levels in the room will be affected by the levels of return air contaminants in the supply air stream. Using a simple differential measurement with respect to the supply air stream would inappropriately cancel out these return air contaminants that legitimately contribute to the levels of air contaminants in room 20. As such a different approach is needed to accurately calculate the indoor air contaminant levels when return air is being used.

Figure 4:
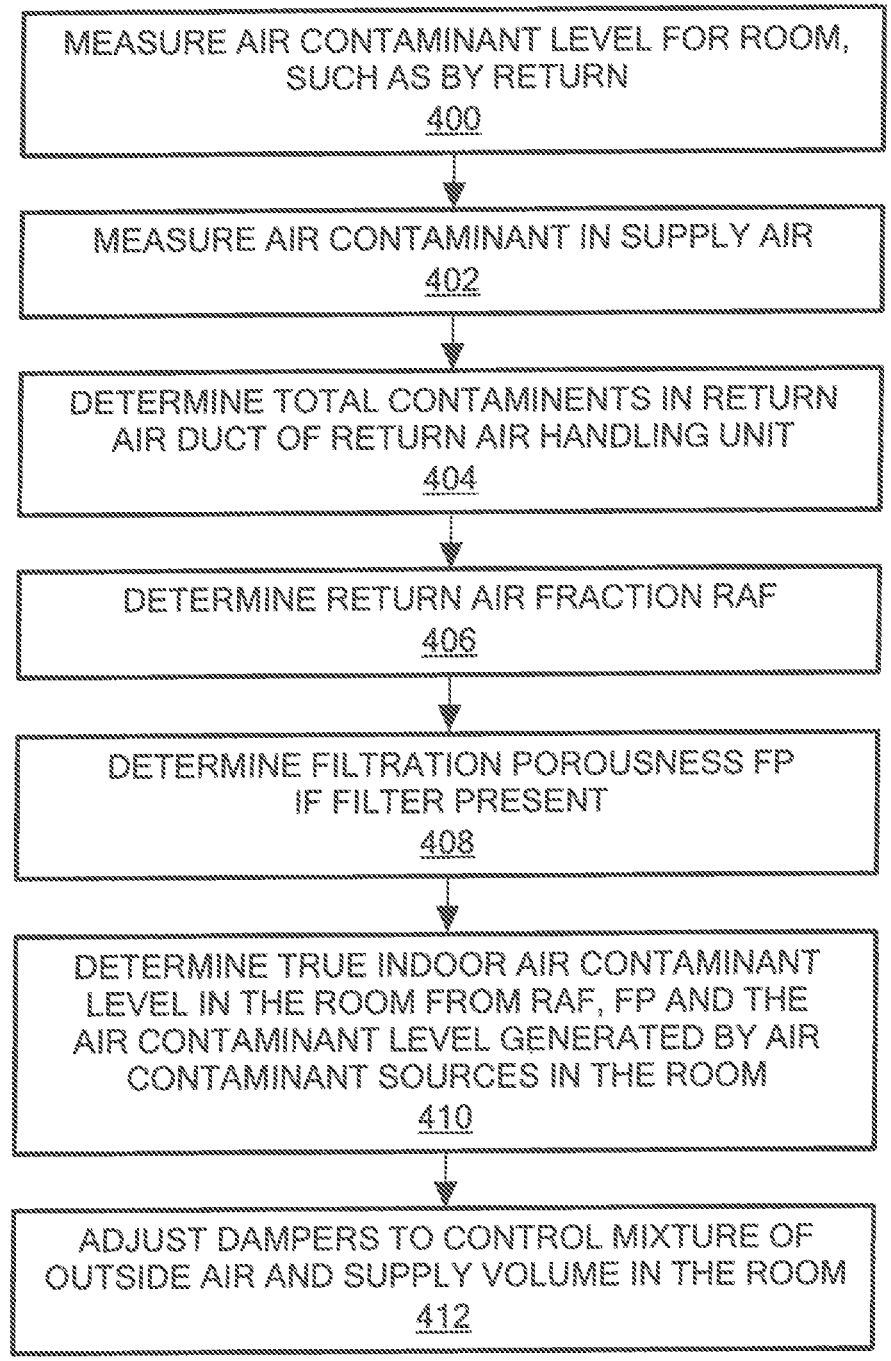
FIG. 4 is a flow diagram showing an exemplary sequence of steps for determining indoor air contaminant levels independent of outdoor contaminant levels.

FIG. 4 shows an exemplary sequence of steps for determining the true indoor air contaminant level in the room. In step 400, the air contaminant level for the room is measured, such as in the room return duct. In step 402, the air contaminant level for the supply air is measured. In step 404, the total contaminants in a return of the return air handling unit is determined. In step 406, the return air fraction (RAF) is computed and in step 408, the filtration porousness (FP) is computed if filters are present. In step 410, the true indoor air contaminant level in the room is computed. In step 412, the dampers in the air handling unit are adjusted to control the mixture of the outside air in the supply air and or the room air flow controller adjusts the amount of supply air volume going into the room using the true indoor contaminant level. The steps are described more fully below.

In terms of determining a method or system to properly calculate the true level of indoor air contaminants in a space one needs to first determine the formula for the return air contaminants in the supply air plus the formula for the contaminants generated in the room. The formula for the air contaminants generated in the room or area 20 to be monitored can be determined by subtracting the total measured air contaminants either in the room 20 itself or its return air duct 40 from the total air contaminant level in the supply air duct 50 or air handler supply location 1037. This can be stated as follows:

$$AC_{R20G} = AC_{R20R} - AC_{R20S}$$

Where:

$AC_{R20G}$ is the air contaminant level generated by air contaminant sources in room 20

$AC_{R20R}$ is the air contaminant level measured in room 20 itself or its room return duct $AC_{R20S}$ is the air contaminant level measured in the supply air duct feeding room 20

The calculation of the indoor air contaminants in the supply air is more complex. We start with the total air contaminants being returned from the room 20 plus other rooms (20A, 20B, 20C, etc) which will be mixed together in the return air 1001 of the return air handler duct. The level of indoor air and outdoor air contaminants or the total contaminants in the return air duct of the return air handling unit 1000 in FIG. 2 is noted as $AC_{AHUR}$ and can be calculated using a weighted average of the total air contaminants in the individual rooms feeding the return air handler based on the return air flow volumes from each of these rooms. The can be represented in a formula as the following for a situation involving three rooms 20A, 20 B, and 20C but where the formula can also be adapted to any number of rooms by adding more terms representing other rooms:

$$AC_{AHUR}=[(AC_{R20AR} \times AV_{R20AR})+(AC_{R20BR} \times AV_{R20BR})+(AC_{R20CR} \times AV_{R20CR})] \div (AV_{R20AR}+AV_{R20BR}+AV_{R20CR})$$

Where:

$AC_{AHUR}$ is the air contaminant level in return air handling unit 1000 return air 1001

$AC_{R20AR}$ is the air contaminant level measured in room 20A itself or its room return duct $AC_{R20BR}$ is the air contaminant level measured in room 20B itself or its room return duct $AC_{R20CR}$ is the air contaminant level measured in room 20C itself or its room return duct $AV_{R20AR}$ is the return air volume from room 20A $AV_{R20BR}$ is the return air volume from room 20B $AV_{R20CR}$ is the return air volume from room 20C An alternate technique for determining the air handling unit's total return air contaminant level, $AC_{AHUR}$, is to actually measure it directly with either discrete air contaminant sensor 1021 or air sampling location 1031 in the air handling unit's return air duct. A percentage of this air contaminant level will make it into the mixed air 1009 of the return air handling unit with rest being exhausted in the return air handling unit's exhaust air 1004. This percentage or fraction is referred to as the return air fraction or RAF. The return air fraction is also equal to one minus the outside air fraction or the fraction of air in the mixed air that is the outside air. Since all of the mixed air goes through the air handling unit and becomes supply air these two fractions also represent the fraction or percentage of return air and outside air in the supply air.

The return air fraction can be determined in one of several ways. For example the sum of the air flow volumes of the recirc air 1005 and outside air 1007 equals the supply air 1014. Therefore if any two of these three airflow volumes are measured either or both of the return air fraction or outside air fraction can be computed. For example the return air fraction equals the Recirc air 1005 air volume divided by the supply air 1014 volume. However the return air fraction also equals one minus the outside air 1007 volume divided by the supply air 1014 air volume. In equation form this is as follows:

$$RAF = AV_{AHURC} \div AV_{AHUS}$$

$$RAF = 1 - (AV_{AHUO} \div AV_{AHUS})$$

Where:

RAF is the return air fraction $AV_{AHURC}$ is the Recirc air 1005 air volume $AV_{AHUS}$ is the supply air 1014 air volume $AV_{AHUO}$ is the outside air 1007 air volume The air volumes mentioned above can be measured automatically and continuously for example with at least two of either the discrete air flow sensor 2031 located in the recirc air duct to measure the recirc air volume 1005, discrete air flow sensor 1023 located in the outside air duct to measure the outside air volume 1007, or discrete air flow sensor 1027 located in the supply air duct to measure the supply air volume 1014. The calculations mentioned above can be done by the data or signal processing unit 1130. Alternatively if the return air fraction is relatively fixed, the return air fraction may be computed on a one time or periodic basis with either two of the installed airflow sensors 2031, 1023, or 1027. Alternatively the flow measurements may be done manually with handheld flow measuring instruments making flow measurements in the ducts of interest and the calculations done manually or by a computer or calculator.

Since flow measurements particularly in the recirc air or outside air ducts may be difficult or expensive, one embodiment includes calculating the return air fraction by using a mass balance measurement approach. The method involves making measurements of some air quality parameter such as temperature or carbon dioxide or some other gas or a particulate in the return air 1001, outside air 1007 and the supply air 1014. Sensing location 1031 or discrete air quality parameter sensor 1021 may be used to measure the air quality parameter in the return air 1001 duct. Sensing location 1033 or discrete air quality parameter sensor 1023 may be used to measure the air quality parameter in the outside air 1007 duct. Finally, sensing location 1037 or discrete air quality parameter sensor 1027 may be used to measure the air quality parameter in the supply air 1014 duct. However, in the case of using temperature as the air quality parameter, since the return air handling unit's heating and cooling coils can affect the measurement of temperature in the supply duct, it is preferred to measure the temperature in the mixed air 1009 duct with temperature sensor 1025. Similarly if particulates or another parameter that may be affected by the final filters in the air handling unit is used for the mass balance unit then the mixed air 1009 should be used as well with sensing done by mixed air sampling location 1035.

The formula for a mass balance calculation to compute either the return or outside air fraction is set forth below:

$$RAF: 1-[(AQP_{AHUR}-AQP_{AHUS}) \div (AQP_{AHUR}-AQP_{AHUO})]$$

Where:

RAF is the return air fraction $AQP_{AHUR}$ is the air quality parameter measured in the return air 1001

$AQP_{AHUS}$ is the air quality parameter measured in the supply air 1014

$AQP_{AHUO}$ is the air quality parameter measured in the outside air 1007

It is important to note that when using carbon dioxide for the mass balance calculation of above that there may be times when the amount of carbon dioxide in the building will be close to or about the same value as the outdoor value. This may be due perhaps to the lack of occupancy in the building, such as during overnight periods or weekends, resulting in the indoor CO2 levels dropping to about the same value as the outdoor value. As the return, supply and outdoor air CO2 values become close together the differential values being calculated in the mass balance calculation of above become small and the accuracy of the calculation will drop.

The use of a multipoint air sampling system with its central or shared sensor can help maintain accuracy with small CO2 differences by at least cancelling out the CO2 sensor's drift error; however there are other error sources that can still become significant for very low CO2 differential measurements. As a result, for values of the return to outside air CO2 difference below some value such as 20 or perhaps even 50 PPM, the calculation may need to be suspended and another value for the return air fraction used. For example the last known or calculated value might be used or the average value over the last few hours. Depending on how constant or variable this fraction is could also determine the best approach for calculating or selecting the value of the return air fraction during these periods of low occupancy or low return to outside air CO2 difference. Alternatively temperature, another air quality parameter, or airflow measurements, may be used during these periods of low return to outside air CO2 difference to compute the return air fraction.

The next factor that is determined, at least with return air handling units that have a filter 1008 that provides at least some amount of filtration of the indoor air contaminant to be measured, is the filter's filtration porousness or FP. This term equals one minus the filtration efficiency for the air contaminant of interest and can be calculated in different ways on a one time, periodic, or continuous basis. First of all if there is no filter or the filter passes near to or 100% of the indoor air contaminant of interest then the filtration porousness is equal to or about 1.0. Otherwise, one way to calculate the filtration porousness is to make measurements of the total indoor air contaminant before and after the filter. This would involve making air contaminant measurements in the mixed air 1009 with sensing location 1035 or discrete air quality parameter sensor 1025 and in the supply air after the filter with sensing location 1037 or discrete air quality parameter sensor 1027. The filter's filtration porousness or FP is then equal to the following:

$$FP = AC_{AHUS} \div AC_{AHUM}$$

Where:
FP is the filter 1008's filtration porousness
$AC_{AHUM}$ is the air contaminant parameter measured in the air handler's mixed air 1009
$AC_{AHUS}$ is the air contaminant parameter measured in the air handler's supply air 1014

Although the above equation is relatively straightforward, in reality the required measurement of the air contaminant in the mixed air can be quite difficult and lacking in accuracy. This is because the outside and return flows of the return air handling unit combine in a relatively small space in the mixed air plenum of the air handling unit and stratification often occurs where the two air streams do not mix well. The air flow becomes well mixed by the time the air exits the air handler in the supply air stream 1014; however in the mixed air plenum it is hard to find a location to measure where the streams of return and outside air are well mixed or combined. The result is an inaccurate mixed air plenum air contaminant measurement. To avoid this problem, one embodiment uses the above calculated return air fraction to compute the mixed air plenum air contaminant measurement or the air contaminant level entering or before the filter 1008. This can be done using a weighted average measurement of the contaminants in the return air 1001 and outside air 1007 air streams. The calculation for FP then becomes as follows:

$$FP = AC_{AHUS} \div \{[RAF \times AC_{AHUR}] + [(1-RAF) \times AC_{AHUO}]\}$$

Where:
FP is the filter 1008's filtration porousness
$AC_{AHUR}$ is the air contaminant level in return air handling unit's return air 1001
$AC_{AHUO}$ is the air contaminant level in return air handling unit's outside air 1007
$AC_{AHUS}$ is the air contaminant level in return air handling unit's supply air 1014

The above measurement of FP is best done continuously since a filter can load up and change its porousness over time. However if the filter's porousness is deemed to be reasonably constant either for example because the filters are changed frequently or the filter has a characteristic where it's porousness does not change much as it loads up then the above measurement can be done on a one time basis with the sampling locations or discrete sensors of FIG. 2 or with the use of handheld instruments. Alternatively, the manufacturer's specifications for filtration efficiency or filtration porousness for the air contaminant of interest may be used if such value is deemed to be reasonably accurate.

Based on the above measurements and calculations we can determine the amount of air contaminant in the return air that passes into the supply air. On an instantaneous basis this is equal to the following equation:

$$RAC_{AHUS} = AC_{AHUR} \times RAF \times FP$$

Where:
$RAC_{AHUS}$ is the level of return air contaminant that passes into the supply air 1014
$AC_{AHUR}$ is the air contaminant level in return air handling unit's return air 1001
FP is the filter 1008's filtration porousness
RAF is the return air fraction Knowing the amount of total return air contaminant passing into the supply air stream is not enough to discriminate the indoor air contaminant level from the outdoor air contaminant level in the supply air stream and in the room of interest since firstly the return air contaminant level includes some outdoor air contaminant as well. Secondly the generation of air contaminants in the room affects the total level of these indoor contaminants in the building and the supply system on a dynamic basis. As calculated above, a fraction of the generated indoor air contaminant that returns to the air handler will be sent back to the room in the supply air. The room air then will then include newly generated contaminants plus a fraction of the previously generated contaminants. The new combined room air will subsequently be sent back again to the return air handling unit where a portion of the combined total return air contaminants will again be fed into the supply air. This set of contaminants will again go into the room where the newly generated contaminants will be added to what is now a fraction of the previous two sets of generated contaminants. As such the generated room indoor air contaminants will go around and around and the indoor air contaminant level will potentially reach some sort of an asymptotic or final value after a period of time. This continuing recirculation of the contaminants makes the potential solution to determine the true indoor air contaminant levels no longer a simple difference calculation or a calculation involving the static amount of total return or even generated room air contaminant in the supply air.

The process of the generated room air contaminant recirculating in the building as it goes through the air handler and back to the room can however be defined by an infinite power series as shown below to define the true indoor air contaminant level in the room:

$$IAC1 = AC_{R20G} + [AC_{R20G} \times (RAF \times FP)] + [AC_{R20G} \times (RAF \times FP)^2] + [AC_{R20G} \times (RAF \times FP)^3] + \ldots + [AC_{R20G} \times (RAF \times FP)^n]$$

Or this can be simplified to $$IAC1 = AC_{R20G} \times [1 + (RAF \times FP) + (RAF \times FP)^2 + (RAF \times FP)^3 + \ldots + (RAF \times FP)^n]$$

Where:
IAC1 is the true indoor air contaminant level in the room 20 when there is only one room
$AC_{R20G}$ is the air contaminant level generated by air contaminant sources in room 20
n is the power of a the RAF×FP term that goes to infinity
FP is the filter 1008's filtration porousness
RAF is the return air fraction Again as noted above this equation represents an infinite power or geometric series with an infinite number of terms. Since the RAF×FP product term will always be less than one this infinite geometric series is known to mathematicians to converge to a finite mathematical solution equal to the following final equation to easily solve for the true indoor air contaminant levels:

$$IAC1 = AC_{R20G} \times \{1 \div [1-(RAF \times FP)]\}$$

Where:

IAC1 is the true indoor air contaminant level in the room 20 when there is only one room $AC_{R20G}$ is the air contaminant level generated by air contaminant sources in room 20

FP is the filter 1008's filtration porousness

RAF is the return air fraction

This equation defines the asymptotic or final value that will be reached after some value of time in the room 20 for a given level of generated contaminants and a given return air fraction and filtration porousness of the return air handling unit's filter 1008. This equation assumes all the contaminant is coming from one room or there is only one room connected to the air handler. If there are multiple rooms (20A, 20B, 20C, or more) on the same return air handling unit and a plurality of rooms can have generated room air contaminants then the equation for the true indoor air contaminant level in a given room (20A, 20B, 20C, or more) must be defined by an equation that also reflects the individual air contaminants generated in all the rooms that contribute to the amount of air contaminants in the return air handling unit's return and supply air streams. There are many ways that these individual indoor air contaminant contributions could be combined for example using the principles of superposition. A preferred embodiment however uses a direct measurement of the return air 1001 in the return air handling unit since it already reflects the weighted average contributions of all of the rooms' internally generated contaminants as was shown above. Therefore the following is a simpler and more general means of computing the indoor air contaminant in a given room when any number of other rooms are involved or even just the one room 20:

$$IACM = AC_{R20G} + (AC_{AHUR} - AC_{AHUS}) \times \{1 \div [1-(RAF \times FP)]\} - (AC_{AHUR} - AC_{AHUS})$$

Or it can be simplified to:

$$IACM = AC_{R20G} + (AC_{AHUR} - AC_{AHUS}) \times \{(RAF \times FP) \div [1-(RAF \times FP)]\}$$

Where:

IACM is the indoor air contaminant level in room 20 with one or multiple rooms used $AC_{R20G}$ is the air contaminant level generated by air contaminant sources in room 20

$AC_{AHUR}$ is the total air contaminant level in return air handling unit's return air 1001

$AC_{AHUS}$ is the total air contaminant level in return air handling unit's supply air 1014

FP is the filter 1008's filtration porousness

RAF is the return air fraction

For simplicity we can define the return air contaminant fraction or RACF as the following:

$$RACF = RAF \times FP$$

Where:

RACF is the return air contaminant fraction

FP is the filter 1008's filtration porousness

RAF is the return air fraction

Using the RACF term allows us to more simply define the two forms of the indoor air contaminant relationship as follows using the previously defined terms:

$$IAC1 = AC_{R20G} \times [1 \div (1-RACF)]$$

Or even more simply as:

$$IAC1 = AC_{R20G} \div (1-RACF)$$

And the more general form where either one or multiple rooms are involved:

$$IACM = AC_{R20G} (AC_{AHUR} - AC_{AHUS}) \times [RACF \div (1-RACF)]$$

The above equations as well as all the preceding equations can be calculated and implemented by the data or signal processing unit 1130 using data calculation methods known to those skilled in the art. Equivalently the building control system 180 may also be used to perform these calculations or another computing device such as perhaps even a remote computing unit connected via the Internet connection 2000 may be used to perform these calculations to derive the indoor air contaminant level of room 20 independent of the outdoor air contaminant levels.

Figure 5:
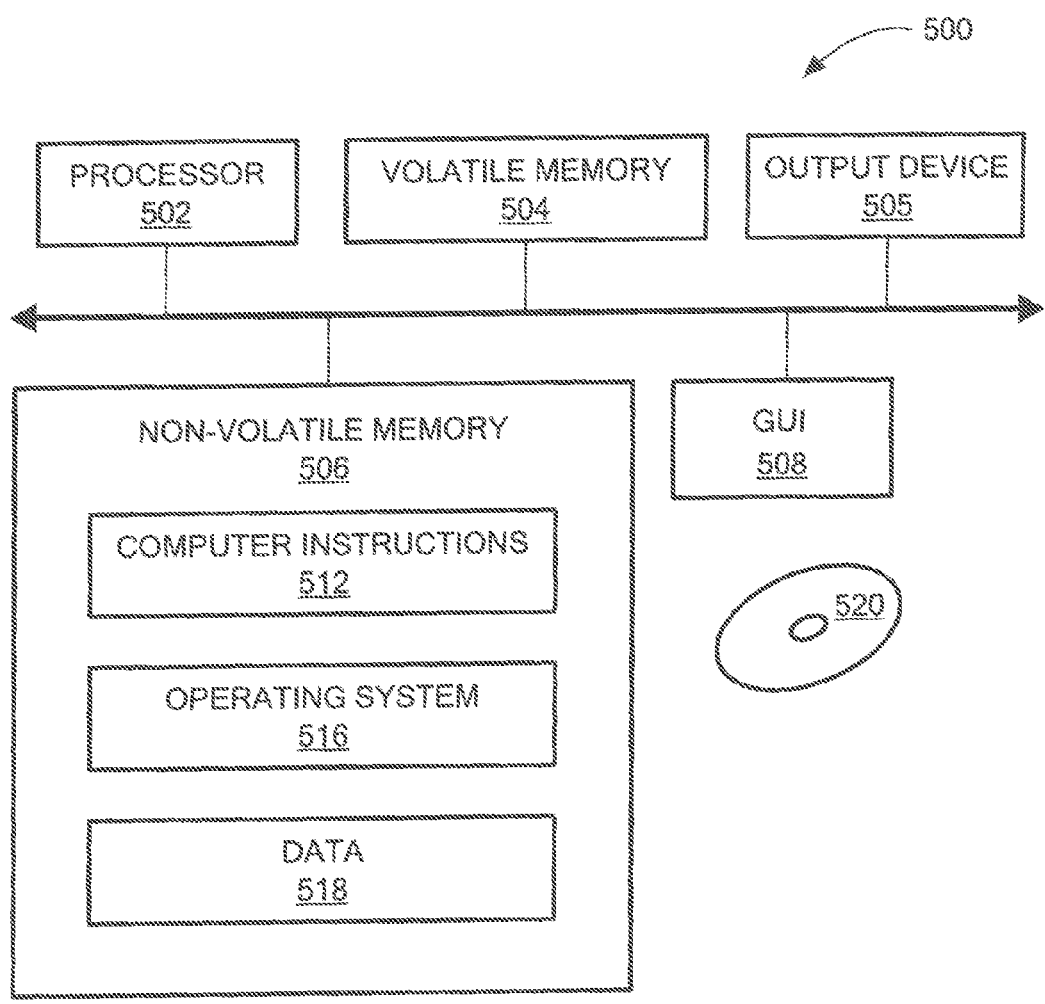
FIG. 5 is schematic representation of an exemplary computer that can perform at least a portion of the processing described herein.

FIG. 5 shows an exemplary computer 500 that can perform at least a portion of the processing described herein. The computer includes a processor 502, a volatile memory 504, a non-volatile memory 506 (e.g., hard disk), an output device 505, and a graphical user interface (GUI) 508 (e.g., a mouse, a keyboard, a display, for example). The non-volatile memory 506 stores computer instructions 512, an operating system 516 and data 518 including the Q files, for example. In one example, the computer instructions 512 are executed by the processor 502 out of volatile memory 504 to perform all or part of the processing. An article 520, such as a disc, can comprise a computer-readable having stored instructions that enable the computer to perform processing described herein.

Processing is not limited to use with the hardware and software shown; processing may find applicability in any computing or processing environment and with any type of machine or set of machines that is capable of running a computer program. Processing may be implemented in hardware, software, or a combination of the two. Processing may be implemented in computer programs executed on programmable computers/machines that each includes a processor, a storage medium or other article of manufacture that is readable by the processor (including volatile and non-volatile memory and/or storage elements), at least one input device, and one or more output devices. Program code may be applied to data entered using an input device to perform processing and to generate output information.

The system may be implemented, at least in part, via a computer program product, (e.g., in a machine-readable storage device), for execution by, or to control the operation of, data processing apparatus (e.g., a programmable processor, a computer, or multiple computers)). Each such program may be implemented in a high level procedural or object-oriented programming language to communicate with a computer system. However, the programs may be implemented in assembly or machine language. The language may be a compiled or an interpreted language and it may be deployed in any form, including as a stand-alone program or as a module, component, subroutine, or other unit suitable for use in a computing environment. A computer program may be deployed to be executed on one computer or on multiple computers at one site or distributed across multiple sites and interconnected by a communication network. A computer program may be stored on a storage medium or device (e.g., CD-ROM, hard disk, or magnetic diskette) that is readable by a general or special purpose programmable computer for configuring and operating the computer when the storage medium or device is read by the computer to perform processing. Processing may also be implemented as a machine-readable storage medium, configured with a computer program, where upon execution, instructions in the computer program cause the computer to operate.

Processing associated with implementing the system may be performed by one or more programmable processors executing one or more computer programs to perform the functions of the system. All or part of the system may be implemented as, special purpose logic circuitry (e.g., an FPGA (field programmable gate array) and/or an ASIC (application-specific integrated circuit)).

Having described exemplary embodiments of the invention, it will now become apparent to one of ordinary skill in the art that other embodiments incorporating their concepts may also be used. The embodiments contained herein should not be limited to disclosed embodiments but rather should be limited only by the spirit and scope of the appended claims. All publications and references cited herein are expressly incorporated herein by reference in their entirety.

What is claimed is:

1. A system for determining indoor air contaminant levels independent of outdoor contaminant levels, comprising:
   an air contaminant monitoring system comprising:
      a first air contaminant sensor for collecting air contaminant levels from at least one partially enclosed area that is served by at least one return air handling unit that mixes at least a portion of building air returned to the air handler air into supply air;
      a second air contaminant sensor for collecting air contaminant levels from the supply air outlet of said return air handling unit; and
      at least one processor configured to:
         determine a return air contaminant fraction from the level of return air inlet contaminants of said return air handling unit that are present in said return air handling unit supply air outlet and the level of the air contaminants in the return air inlet; and
         process at least one indoor air contaminant parameter from:
            a magnitude of the difference between the air contaminant levels of said partially enclosed area and said supply air outlet of said return air handling unit feeding said partially enclosed area; and
            said return air handling unit return air contaminant fraction.

2. The system of claim 1, wherein said indoor air contaminant is a particulate.

3. The system of claim 2, wherein said particulate includes environmental tobacco smoke.

4. The system of claim 1, wherein said indoor air contaminant comprises a gas.

5. The system of claim 4, wherein said gas comprises a volatile organic compound.

6. The system of claim 1, wherein said air contaminant sensor is part of a multipoint air monitoring system.

7. The system of claim 6, wherein said multipoint air monitoring system is a multipoint air sampling system.

8. The system of claim 1, wherein the processor is further configured to determine the return air contaminant fraction by determining the return air fraction, wherein the return air fraction comprises the percent of the total return air coming back to the return air handling unit that is being mixed with outside air to constitute the air handler supply air.

9. The system of claim 8, wherein determining the return air fraction comprises a one time or periodically measured set of flow measurements, mass balance measurements, or other manual means that are used to compute the return air fraction at least once or periodically.

10. The system of claim 8, wherein determining the return air fraction comprises automatic means to compute either continuously or periodically the return air fraction by using either flow sensing means, mass balance measurement means, or other automatic means.

11. The system of claim 10, wherein the processor is configured to perform a mass balance calculation and;
   wherein the system further comprises a sensor to make carbon dioxide measurements representative of the carbon dioxide values in said return air handling unit return inlet, outside air inlet, and supply air outlet.

12. The system of claim 1, wherein said return air handling unit contains a filter in the return, mixed air, or supply air path capable of some amount of filtering of said air contaminant.

13. The system of claim 1, wherein the processor is further configured to:
   determine the return air fraction;
   determine a filtration porousness of the filter; and
   multiply the return air fraction by the filtration porousness to compute the return air contaminant fraction.

14. The system of claim 13, wherein determining the filtration porousness comprises,
   one or more air contaminant sensing means that senses an air contaminant that is filtered by the filter and takes a one time, periodic, and/or continuous air contaminant measurements of both the air before it enters the filter and the air after it leaves the filter,
   wherein processor is configured to compute the filtration porousness either one time, periodically, or continuously by dividing said air contaminant measurement of the air leaving said filter by said air contaminant measurement of the air entering said filter.

15. The system of claim 13, wherein determining the filtration porousness comprises,
   one or more air contaminant sensing means that senses an air contaminant that is filtered in some manner by the filter and takes a one time, periodic, or continuous air contaminant measurements representative of the air contaminant values in said return air handling unit return air inlet, outside air inlet, and supply air outlet,
   wherein the processor is configured to compute the filtration porousness either one time, periodically, or continuously by dividing said air contaminant measurement representative of the air contaminant values in said return air handling unit's supply air outlet by the sum of two terms,
   wherein, the first term is equal to the product of said return air fraction times said air contaminant measurement representative of the air contaminant values in said return air handling unit's return air inlet and;
   the second term is equal to the product of one minus said return air fraction times said air contaminant measurement representative of the air contaminant values in said return air handling unit's outside air inlet.

16. The system of claim 1, further comprising,
   at least one airflow control device to control airflow volume either to or from said at least one partially enclosed area; and
   an airflow controller that uses said indoor air contaminant parameter measurement or a signal at least partially determined by said indoor air contaminant parameter measurement to at least partially control airflow volumes to or from one or more of said partially enclosed areas.

17. The system of claim 1, further comprising,
   at least one airflow control device to control the outside air volume entering the outside air inlet of said return air handling unit; and
   an airflow controller that uses said indoor air contaminant parameter measurement or a signal at least partially determined by said indoor air contaminant parameter measurement to at least partially control the outside air volumes entering the outside air inlet of said return air handling unit.

18. The system of claim 1, wherein processor is further configured to:
   take the magnitude of the difference between the air contaminant levels of said partially enclosed area and said supply air outlet of said return air handling unit feeding said partially enclosed area; and
   divide said difference by the term of one minus said return air handling unit return air contaminant fraction.

19. The system of claim 1, further comprising at least one air contaminant sensor for collecting air contaminant levels from the return air inlet or duct of said return air handling unit, wherein the processor is further configured to:
   determine the magnitude of a first difference between the air contaminant levels of said partially enclosed area and said supply air outlet of said return air handling unit feeding said partially enclosed area;
   determine the magnitude of a second difference between the air contaminant levels of said return air inlet or duct and said supply air outlet of said return air handling unit feeding said partially enclosed area;
   determine the magnitude of a first factor calculated from said return air handling unit return air contaminant fraction divided by the term of one minus said return air handling unit return air contaminant fraction; and
   add said first difference to the product of said second difference multiplied by said first factor.

* * * * *